United States Patent
Hur et al.

(10) Patent No.: US 9,845,456 B2
(45) Date of Patent: Dec. 19, 2017

(54) COMPOSITION CONTAINING COMPLEX CYTOKINES DERIVED FROM EBV-INFECTED B CELLS FOR INDUCING THE MATURATION OF DENDRITIC CELLS

(71) Applicant: INJE UNIVERSITY INDUSTRY-ACADEMIC COOPERATION FOUNDATION, Gimhae-si, Gyeongsangnam-do (KR)

(72) Inventors: Dae Young Hur, Busan (KR); Ga Bin Park, Busan (KR); Yeong Seok Kim, Busan (KR); Hyun Kyung Lee, Busan (KR); Dae Jin Kim, Seoul (KR)

(73) Assignee: INJE UNIVERSITY INDUSTRY-ACADEMIC COOPERATION FOUNDATION, Gimhae-si, Gyeongsangnam-Do (KR)

( * ) Notice: Subject to any disclaimer, the term of this patent is extended or adjusted under 35 U.S.C. 154(b) by 17 days.

(21) Appl. No.: 14/220,138

(22) Filed: Mar. 20, 2014

(65) Prior Publication Data
US 2014/0242694 A1  Aug. 28, 2014

Related U.S. Application Data

(63) Continuation of application No. PCT/KR2012/007660, filed on Sep. 24, 2012.

(30) Foreign Application Priority Data

Sep. 23, 2011  (KR) .......................... 10-2011-0096312

(51) Int. Cl.
| | |
|---|---|
| C12N 5/00 | (2006.01) |
| C12N 5/02 | (2006.01) |
| C12N 5/10 | (2006.01) |
| C12N 5/0784 | (2010.01) |
| C07K 14/54 | (2006.01) |

(52) U.S. Cl.
CPC ............ *C12N 5/0639* (2013.01); *C07K 14/54* (2013.01); *C12N 2501/2301* (2013.01)

(58) Field of Classification Search
None
See application file for complete search history.

(56) References Cited

U.S. PATENT DOCUMENTS 5,866,115 A  2/1999  Kanz et al.

FOREIGN PATENT DOCUMENTS

| EP | 0663930 B1 | 9/1998 |
|---|---|---|
| EP | 0922758 B1 | 4/2009 |
| KR | 10-2010-0109099 A | 10/2010 |
| WO | 95/28479 A1 | 10/1995 |

OTHER PUBLICATIONS

Zou et al. Cytokines in the generation and maturation of dendritic cells: recent advances. European Cytokine Network, 2002; 13(2): 186-199.*
Allavena et al. IL-10 prevents the differentiation of monocytes to dendritic cells but promotes their maturation to macrophages. European Journal of Immunology. 1998, 28:359-369.*
Schenk et al. Interleukin-1b triggers the differentiation of macrophages with enhanced capacity to present mycobacterial antigen to T cells. Immunology, 2014; 141(2):174-180.*
Miyauchi, K., et al. "Cytokine signatures of transformed B cells with distinct Epstein-Barr virus latencies as a potential diagnostic tool for B cell lymphoma." Cancer Sci., Jun. 2011, vol. 102, No. 6, pp. 1236-1241.
Yurchenko, M., et al. "CD150-mediated Akt signalling pathway in normal and malignant B cells." Exp. Oncol., Mar. 2011, vol. 33, No. 1, pp. 9-18.
Ferrand, V., et al., "Absence of SLAM mutations in EBV-associated lymphoproliferative disease patients." J. Med. Virol., May 2003, vol. 70, No. 1, pp. 131-136.
Muraba Yashi, N., et al. "Susceptibility of human dendritic cells (DCs) to measles virus (MV) depends on their activation stages in conjunction with the level of CDw 150: role of Toll stimulators in DC maturation and MV amplification.", Microbes Infect., Jul. 2002, vol. 4, No. 8, pp. 785-794.
Kayo Inaba., et al. "Dendritic cell progenitors phagocytose particulates, including bacillus Calmette-Guerin organisms, and sensitize mice to mycobacterial antigens in vivo." JEM., Aug. 1, 1993, vol. 178 No. 2, 479-488.
Kayo Inaba., et al. "Dendritic cells as antigen presenting cells in vivo." International Reviews of Immunology, 1990, vol. 6, No. 2-3 : pp. 197-206.
Frank J. Hsu et al., "Vaccination of patients with B-cell lymphoma using autologous antigen-pulsed dendritic cells" Nature Medicine., Jan. 1996, 2(1), 52-8.

* cited by examiner

*Primary Examiner* — Vanessa L Ford
*Assistant Examiner* — Sandra Dillahunt
(74) *Attorney, Agent, or Firm* — Revolution IP, PLLC

(57) ABSTRACT

A composition for deriving the maturation of dendritic cells includes complex cytokines generated by the simulation, the expression of which is induced on EBV-infected B cells. The dendritic cell maturation process, which conventionally takes approximately 7 days, can be shortened to 2 days, thereby producing dendritic cells in a more economically advantageous and effective manner.

1 Claim, 19 Drawing Sheets

COMPOSITION CONTAINING COMPLEX CYTOKINES DERIVED FROM EBV-INFECTED B CELLS FOR INDUCING THE MATURATION OF DENDRITIC CELLS

CROSS REFERENCE TO PRIOR APPLICATIONS

This application is a Continuation Application of PCT International Patent Application No. PCT/KR2012/007660 filed on Sep. 24, 2012, under 35 U.S.C. §371, which claims priority to Korean Patent Application No. 10-2011-0096312 filed on Sep. 23, 2011, which are all hereby incorporated by reference in their entirety.

BACKGROUND

The present invention relates to a use of complex cytokines in the maturation of dendritic cells, wherein the complex cytokines are produced by the stimulation of CD150, the expression of which is induced in EBV-infected B cells, and a method of preparing dendritic cells by using the use.

Dendritic cells are the strongest antigen presenting cells, and although they exist in small quantities in vivo, their controlling capability of T cell immunity are excellent. Also, when dendritic cells isolated from tissue or blood are stimulated by an antigen in vitro and then injected in vivo in the form of mature dendritic cells, the dendritic cells show immunogenicity. Accordingly, the dendritic cells are highly suitable for use as a cell vaccine for inducing immunity to specific antigens of tumor or pathogen (Inaba, K. et al., 3. Exp. Med., 178:479, 1993; Inaba, K. et al., Int. Rev. Immunol., 6:197, 1990; Hsu, F. et al., Nature Med., 2:52, 1996).

Techniques for obtaining and maturing dendritic cells are disclosed in many disclosures: mature dendritic cells are produced from immature dendritic cells derived from pluripotent cells that express either microphage characteristics or dendritic cell characteristics, wherein immature dendritic cells are brought in contact with a dendritic cell maturation factor comprising IFN-α (European Patent No. 922,758); Human CD34+ hemoblast is cultured with (i) GM-CSF, (ii) TNF-α and IL-3, or (iii) GM-CSF and TNF-α to induce the formation of CD1a+ hemoblast, and from the culture, CD1a+ human dendritic cells are harvested (European Patent No. 663,930); and peripheral blood cells are isolated and enriched in blood precursor cells that express CD34 antigen, and the cells are multiplied with hematopoietic growth factors associated with cytokines (WO 95/28479).

CD150 (also known as signaling lymphocyte activation molecule (SLAM)) is a type I trans-membrane glycoprotein belonging to the CD2/CD150 family of the immunoglobulin superfamily of proteins. In humans, CD150 is constitutively expressed on immature thymocytes and CD45RO+ memory T cells, and is considered as a molecule playing an important role in cell adhesion and signaling in the immune synapse between T cells and antigen-presenting cell (APC).

High levels of CD150 expression are frequently associated with B cell malignancies, and recently, many study results on effects of CD150 on intracellular signaling and the secretion of cytokines are being reported.

The inventors of the present invention found that CD150 expression increases on EBV-infected B cells, and based on the founding, they researched into how CD150 acts on EBV-infected B cells. As a result, the inventors confirmed that due to the stimulation of CD150, production of complex cytokines is derived in EBV-infected B cells, and such complex cytokines are used to rapidly produce mature dendritic cells from monocytes, thereby completing the present invention.

SUMMARY

One or more embodiments of the present invention provide a method of efficiently and rapidly producing dendritic cells that are suitable for use as a cell vaccine for inducing immunity to a specific antigen of tumor or pathogen, wherein complex cytokines induced in EBV-infected B cells are used to produce mature dendritic cells.

According to an aspect of the present invention, a composition for deriving mature dendritic cells, wherein the composition includes complex cytokines produced by the stimulation of CD150, the expression of which is induced on EBV-infected B cells.

According to an aspect of the present invention, a method of producing dendritic cells includes: isolating a monocyte from human peripheral blood mononuclear cells (PBMC); and treating the monocyte with complex cytokines produced by the stimulation of CD150 of which expression is induced on EBV-infected B cells.

According to embodiments of the present invention, a dendritic cell maturation process, which conventionally takes approximately 7 days, can be shortened to 2 days, thereby producing dendritic cells in a more economically advantageous and effective manner.

BRIEF DESCRIPTION OF DRAWINGS

FIG. 13 shows ELISA analysis results on cytokines generated according to CD150 stimulating molecules, in EBV-infected B cells.

FIG. 14 shows ELISA analysis results on cytokines generated according to CD150 stimulating molecules, in Raji cells.

DETAILED DESCRIPTION

Figure 1:
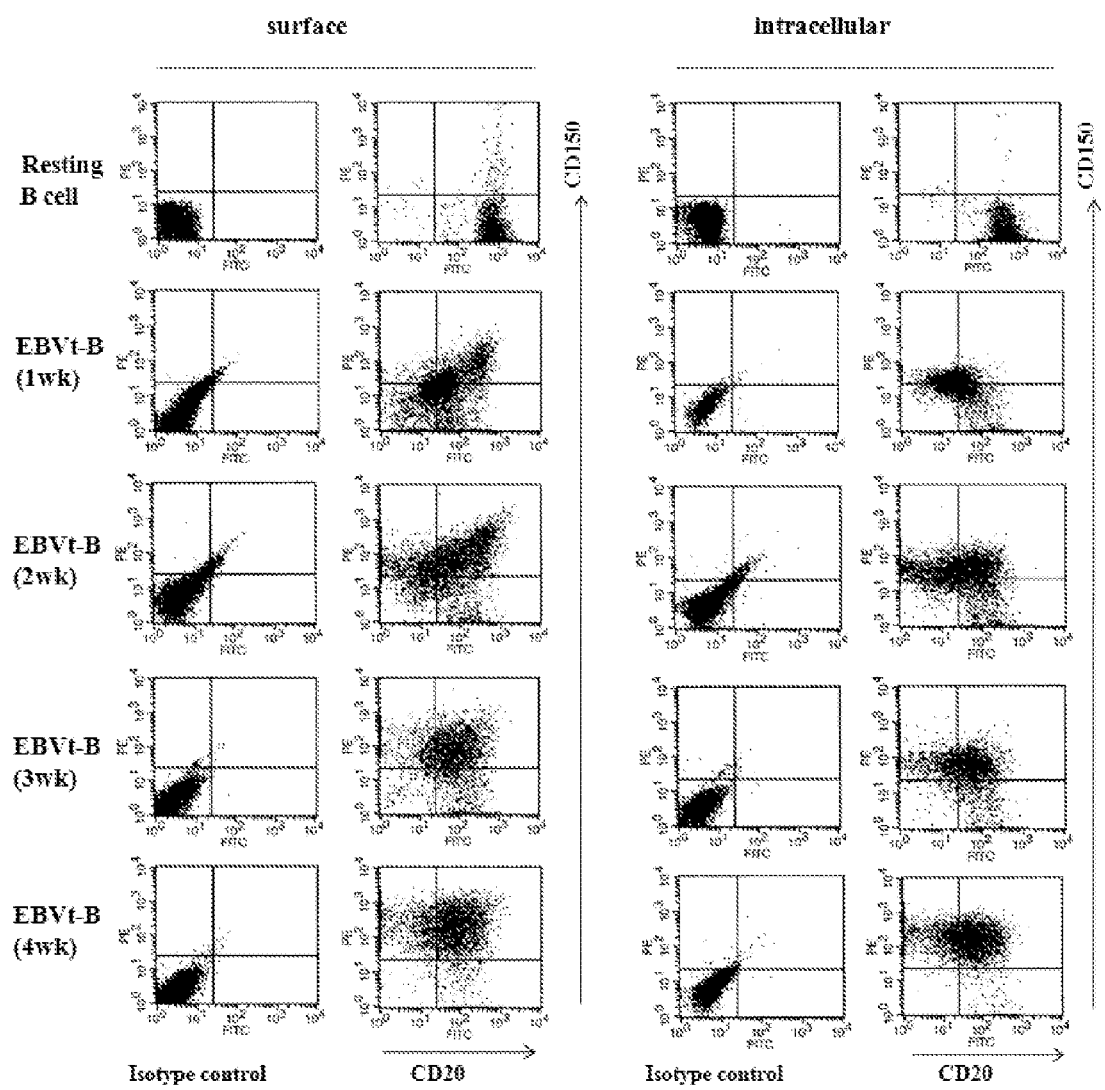
FIG. 1 shows flow cytometric results showing expression of CD150 on B cells infected with EBV.

One or more embodiments of the present invention provide a composition for deriving the maturation of dendritic cells, wherein the composition includes complex cytokines generated by the simulation of CD150, the expression of which is induced on EBV-infected B cells.

In an embodiment of the present invention, when B cells are cultured with EBV supernatant obtained in EBV B95-8 marmoset cell lines, B cells are transformed into EBV-infected B cells, expressing CD150 in great quantities on their surfaces.

Inventors of the present invention found that when CD150, the expression of which is induced on EBV-infected B cells, is stimulated, production of complex cytokines is induced, and when a monocyte is treated with such complex cytokines, the monocyte is rapidly differentiated into dendritic cells, thereby completing the present invention.

The complex cytokines exist in a culture supernatant of EBV-infected B cells with CD150 stimulated, and comprise at least one of IL-1A, IL-1B, IL-4, IL-5, IL-6, IL-8, IL-10, IL-12, IL-17A, and GM-CSF.

In another embodiment of the present invention, CD150 may be stimulated by antigen-antibody binding caused by anti-CD150 antibody. In other embodiments, a recombinant protein bindable to CD150 or a virus fragment using CD150 as a receptor for cellular entry may be used to bind to CD150, stimulating CD150 to activate intracellular signaling of EBV-infected B cells with expressed CD150 thereon.

An example of the virus using CD150 as a receptor for cellular entry is Measles virus, but is not limited thereto.

According to another aspect of the present invention, a method of producing dendritic cells includes: isolating a monocyte from human peripheral blood mononuclear cells (PBMC); and treating the monocyte with complex cytokines produced by the stimulation of CD150 of which expression is induced on EBV-infected B cells.

In an embodiment, the isolating of monocyte may be performed by MACS or a plastic adherent method, but the isolating method is not limited thereto.

In detail, a plastic adherent method may be performed as follows: PBMC is placed together with an animal serum medium in a culture vessel and incubated for 1 to 6 hours to adhere a monocyte, and non-adherent cells are removed therefrom to obtain the monocyte. MACSTo may be performed to obtain higher purity of monocyte as follows: PBMC is reacted with CD14, CD3, or CD19 antibody and then passed through a column to obtain pure single cell. However, the isolating method is not limited thereto.

In other embodiments, the complex cytokines exist in a culture supernatant of EBV-infected B cells with CD150 stimulated, and comprise at least one of IL-1A, IL-1B, IL-4, IL-5, IL-6, IL-8, IL-10, IL-12, IL-17A, and GM-CSF.

Accordingly, in an embodiment, in the treating monocyte with complex cytokines, a monocyte may be treated with complex cytokines by the treatment with a culture supernatant of EBV-infected B cells.

In an embodiment, CD150 may be stimulated by antigen-antibody binding caused by anti-CD150 antibody, or by using recombinant protein bindable to CD150 or a virus fragment using CD150 as a receptor for cellular entry to bind to CD150, to activate intracellular signaling of EBV-infected B cells having CD150 expressed to induce the formation of cytokines.

Hereinafter, one or more embodiments of the present invention will be explained in detail for better understanding. However, the following embodiments are provided herein for illustrative purpose only, and do not limit the scope of the present invention. Embodiments of the present invention are provided to one of ordinary skill in the art for the complete understanding of the present invention.

Experimental Example

The following experimental examples are commonly applied Examples.

1. Preparation of EBV Infectious Virion and Generation of EBV-Infected B Cells

EBV supernatant stock was prepared from an EBV B95-8 marmoset cell line. PBMCs were isolated from whole blood of five human volunteers by FICOLL®-paque (Amersham Life Science, Buckinghamshire, England) gradient centrifugation. B cells were purified from PBMCs using a MACS B cell-negative depletion kit (Miltenyi Biotec, Auburn, Calif.). Purified cells were added to EBV stock supernatant, and after 2 h incubation at 37° C., RPMI-1640 medium (HyClone) and 1 mg/ml cyclosporine A (Sigma-Aldrich, St. Louis, Mo.) were added ($5 \times 10^5$ cells/ml). The cultures were incubated for 2 to 4 weeks until clumps of EBV-infected B cells were visible and the medium turned yellow. The phenotype was monitored using a FACSCalibur flow cytometer (BD Biosciences, San Jose, Calif.) using PE-conjugated anti-human anti-CD150 Ab (BD Biosciences) and FITC-conjugated anti-CD20 Ab (BD Biosciences). This study was approved by the Institutional Bioethics Review Board at the Medical College of Inje University, and all donors gave informed consent for the study.

2. Binding of CD150 on EBV-Infected B Cells

Cells (4 weeks, $1 \times 10^6$ cells/14) were harvested and washed twice in cold PBS. Cells were resuspended in 100 μl PBS and incubated with anti-CD150 mAb (clone IPO-3, 1 μg/ml, Affinity Bioreagents, Golden, Colo.) or isotype control (clone UPC-10, 1 μg/ml, Sigma-Aldrich), at 37° C. for 30 min. Cells were washed in PBS and resuspended in 100 μl PBS and then incubated with goat anti-mouse IgG (2 μg/ml, Sigma-Aldrich) for 15 min at 37° C. After cells were washed they were further cultured in RPMI-1640 medium for 24 h at 37° C.

3. CD150 Stimulation by Measles Virus or Recombinant CD150 Protein

Cells (4 weeks, $1 \times 10^6$ cells/ml) were harvested and washed twice in cold PBS. Cells were resuspended in 100 μl PBS and incubated with Measles virus (SEQ ID NO: 33) (399-525 amino acid, MV#1 (SEQ ID NO: 34) or 89-165 amino acid, MV#2 (SEQ ID NO: 35); 1 μg/ml, GenWay, Biotech, Inc., San Diego, Calif.) at 37° C. for 1 h. After cells were washed they were cultured in RPMI-1640 medium for 24 h at 37° C. After cells were washed they were further cultured in RPMI-1640 medium for 24 h at 37° C.

4. Quantification of Human Cytokines by ELISA

Culture supernatant from CD150-stimulated or MV (SEQ ID NO: 33) (MV#1 (SEQ ID NO: 34) or MV#2 (SEQ ID NO: 35); GenWay)-B cells was concentrated using AMICON® Ultra-15 (Millipore, Beverly, Mass.). IL-1A, IL-1B, IL-2, IL-4, IL-5, IL-6, IL-8, IL-10, IL-12A, IL-13, IL-17A, and GM-CSF concentrations in the concentrated 10-fold cell-free culture supernatants were determined by multi-cytokine ELISA assay (Multi-Analyte ELISARRAY™; SABiosciences, Corp, Frederick, Md.) and quantified by Single cytokine ELISA assay (Single Analyte ELISARRAY™; SABiosciences). The data are expressed as the average of the number of biological replicates±standard deviation (SD).

5. Human Monocyte Isolation, Differentiation, and Cell Surface Phenotyping

For monocyte isolation by plastic adherence, $1 \times 10^7$ PBMCs per well were distributed into 6-well plates (BD Biosciences) and allowed to adhere in a 5% $CO_2$ incubator at 37° C. for 4 h in 2 ml complete medium (CM) consisting of RPMI-1640 supplemented with 10% fetal bovine serum, streptomycin, and glutamine at 37° C. in 5% $CO_2$. Non-adherent cells were removed and adherent cells were washed three times with pre-warmed 10% CM. Monocytes were differentiated into DCs by culturing for 7 days in CM with concentrated cell culture supernatant from CD150 stimulated or MV (MV#1 or MV#2; GenWay)-stimulated cells.

The phenotype of cells was monitored using a FACSCalibur flow cytometer (BD Biosciences) and a Confocal Laser-Scanning microscope (Carl Zeiss, Jena Germany) at 400× original magnification using FITC-conjugated anti-human anti-CD14, anti-CD1a, anti-CD80, anti-CD86, anti-CD83, anti-HLA-DR, and anti-CD11c Abs (BD Biosciences). Images were acquired using confocal microscopy software release 3.0 (Carl Zeiss, 510 META).

6. siRNA Synthesis and Transfection

Three different 19nt long interfering RNA duplexes with two 3'end overhang dT nucleotides and negative control siRNA duplexes for either low or medium GC content were obtained from Bioneer (Daejeon, Korea). Three experimentally verified CD150 siRNA sequences were selected from the Bioneer siRNA database. The CD150 siRNA target sequences are listed in Table 1. Non-specific siRNA labeled with green fluorescence was used as a control for validating transfection efficiency for each experiment. Cells were transiently transfected by electroporation under optimized conditions. Briefly, cells were electroporated with 200 nM siRNA in serum-free medium in a 0.4 cm electroporation cuvette using the Bio-Rad Gene Pulser Xcell system (Bio-Rad Laboratories, Hercules, Calif.). In transfection experiments assessing CD150-induced cytokine production, 24 h after transfection cells were either treated or left untreated with anti-CD150 mAb for a period of 24 h. For certain experiments, extracted RNA was analysed by RT-PCR and real-time RT-PCR.

TABLE 1

| Target | Primers, 5 → 3 Sense | Antisense | Product size |
|---|---|---|---|
| CD150 | TAT CTA CAT CTG CAC CGT GAG C (SEQ ID NO: 1) | TCC TGA GCT GGG AAG GAG T (SEQ ID NO: 2) | 288 bp |
| IL-1A | CTG CAT GGA TCA ATC TGT (SEQ ID NO: 3) | CCC ATG TCA AAT TTC ACT GC (SEQ ID NO: 4) | 369 bp |
| IL-1B | CAG CTA CGA ATC TCC GAC CAC (SEQ ID NO: 5) | GGC AGG GAA CCA GCA TCT TC (SEQ ID NO: 6) | 100 bp |
| IL-4 | ATG GGT CTC ACC TCC CAA CTG CTT (SEQ ID NO: 7) | TTT CCA ACG TAC TCT GGT TGG C (SEQ ID NO: 8) | 355 bp |
| IL-5 | TCT GAG GAT TCC TGT TCC TG (SEQ ID NO: 9) | TTA TCC ACT CGG TGT TCA TT (SEQ ID NO: 10) | 248 bp |
| IL-6 | GTG TTG CCT GCT GCC TTC CCT G (SEQ ID NO: 11) | CTC TAG GTA TAC CTC AAA CTC CAA (SEQ ID NO: 12) | 321 bp |
| IL-8 | ATG ACT TCC AAG CTG GCC GTG GCT (SEQ ID NO: 13) | TCT CAG CCC TCT TCA AAA ACT TCT C (SEQ ID NO: 14) | 292 bp |
| IL-10 | CTG AGA ACC AAG ACC CAG ACA TCA AGG (SEQ ID NO: 15) | GTC AGC TAT CCC AGA GCC CCA GAT CCG (SEQ ID NO: 16) | 327 bp |
| IL-12A | CTT CAC CAC TCC CAA AAC CTG (SEQ ID NO: 17) | AGC TCA TCA CTC TAT CAA TAG (SEQ ID NO: 18) | 532 bp |
| IL-12B | CAT TCG CTC CTG CTG CTT CAC (SEQ ID NO: 19) | TAC TCC TTG TTG TCC CCT CTG (SEQ ID NO: 20) | 266 bp |
| IL-17 | ATG ACT CCT GGG AAG ACC TCA TTG (SEQ ID NO: 21) | TTA GGC CAC ATG GTG GAC AAT CGG (SEQ ID NO: 22) | 156 bp |
| GM-CSF | ATG TGG CTG CAG AGC CTG CTG C (SEQ ID NO: 23) | CTG GCT CCC AGC AGT CAA AGG G (SEQ ID NO: 24) | 424 bp |
| β-actin | ATC CAC GAA ACT ACC TTC AA (SEQ ID NO: 25) | ATC CAC ACG GAG TAC TTG C (SEQ ID NO: 26) | 200 bp |

TABLE 1-continued

| Target | Primers, 5 → 3 Sense | Antisense | Product size |
|---|---|---|---|
| CD150-si | GUG UCA UCA UGA UUC UCA U(dTdT) (SEQ ID NO: 27) | AUG AGA AUC AUG AUG ACA C(dTdT) (SEQ ID NO: 28) | siRNA#1 |
| CD150-si | GGU ACC UUA UGA CCC UGG A(dTdT) (SEQ ID NO: 29) | UCC AGG GUC AUA AGG UAC C(dTdT) (SEQ ID NO: 30) | siRNA#2 |
| CD150-si | GAG AUC GCU ACA AGU UUU A(dTdT) (SEQ ID NO: 31) | UAA AAC UUG UAG CGA UCU C(dTdT) (SEQ ID NO: 32) | siRNA#3 |

7. RT-PCR and Real Time RT-PCR

Total RNA was isolated using an RNeasy Mini kit (Qiagen, Hilden, Germany). RNA was transcribed into cDNA using oligo (dT) primers and reverse transcriptase. To investigate apoptosis-associated molecules, PCR amplification was performed using specific primer sets (Bioneer) for CD150, IL-1A, IL-1B, IL-4, IL-5, IL-6, IL-8, IL-10, IL-12A, IL-12B, IL-17, GM-CSF, and β-actin (see Table 1). PCR was performed using Prime Taq Premix (GeNet Bio, Chungnam, Korea). PCR products were analyzed by agarose gel electrophoresis and visualized with ethidium bromide under UV light using the multiple Gel DOC system (Fujifilm, Tokyo, Japan). Quantitative real-time RT-PCR was performed using a single tube SYBR Green kit (Takara, Tokyo, Japan), iCycler thermal real-time PCR system (Bio-Rad), and the same specific primer sets used in conventional RT-PCR. The relative gene expression compared with unstimulated cells was determined by the Mx3000P software's built-in algorithm using an adaptive baseline to determine the Ct. Experiments were performed in triplicate, and data are expressed as mean±SD.

8. Immunoblotting

After stimulation, cells were harvested and lysed in RIPA buffer (Elpis Biotech, Daejeon, Korea) containing a protease inhibitor cocktail (Sigma-Aldrich). To measure phosphorylation events, an additional set of phosphatase inhibitors (Sigma-Aldrich) were added to the RIPA buffer. Protein concentration was determined using a BCA assay kit (Pierce, Rockford, Ill.). Proteins (10 μg/sample) were heated for 5 min at 100° C. Total cell lysates ($5 \times 10^6$ cells/sample) were electrophorized to SDS-PAGE on a gel containing 10% or 15% (w/v) acrylamide under reducing conditions. Separated proteins were transferred to nitrocellulose membranes (Millipore), the membranes were blocked with 5% skim milk, and commercial Western blot analysis was performed. Chemiluminescence was detected using an ECL kit (Amersham Life Science) and the multiple Gel DOC system (Fujifilm). The following primary antibodies were used: β-actin, SAP (SH2D1A), phospho-Lyn ($Tyr^{507}$), Lyn, Fyn, SHIP, phospho-Src ($Tyr^{416}$), and Src from Cell Signaling Technology (Beverly, Mass.); phospho-CD150 ($Tyr^{281}$) from Santa Cruz Biotechnology (Delaware, Calif.); and phospho-Fyn ($Y^{530}$) from Abcam (Cambridge, UK).

9. Immunoprecipitation (IP) and Co-Immunoprecipitation (Co-IP) Assay

After stimulation, cells ($1 \times 10^7$ cells/sample) were harvested and lysed in RIPA buffer (Elpis Biotech) containing a protease inhibitor cocktail (Sigma-Aldrich). To measure phosphorylation events, an additional set of phosphatase inhibitors (Sigma-Aldrich) were added to the RIPA buffer. To reduce non-specific binding of protein, lysates were pre-cleared by incubating them with washed protein A PLUS-agarose beads (Santa Cruz Biotechnology). For IP, precleared lysate was added to the recommended amount of anti-CD150 antibody and incubated at 4° C. for 2 h on a rotator. Then, the immunoprecipitates were harvested using protein A PLUS-agarose beads (Santa Cruz Biotechnology) by being incubated at 4° C. for 2 h under rotary agitation. After incubation, the supernatant was removed and the beads were washed in lysis buffer four times. Finally, immunoprecipitates were eluted by boiling the beads in SDS-PAGE sample buffer for 5 min and then characterized by Western blotting with appropriated antibodies.

<Example 1> CD150 Expression on B Cells is Induced by EBV Infection

EBV-infected B cells were harvested every 4 weeks after the infection. Cell phenotype was observed by flow cytometry and confocal microscopy (data not shown).

Results are shown in FIG. 1.

Referring to FIG. 1, it was confirmed that CD150 was minimally expressed on the surface and in the cytoplasm of CD20+ resting B cells. Expression of CD150 gradually increased during the first week following infection and was then quickly elevated. After 4 weeks of EBV infection, CD150 expression had significantly increased in transformed B cells; most of the EBV-infected B cells strongly expressed CD150 molecules on the surface and in the cytoplasm.

Figure 2:
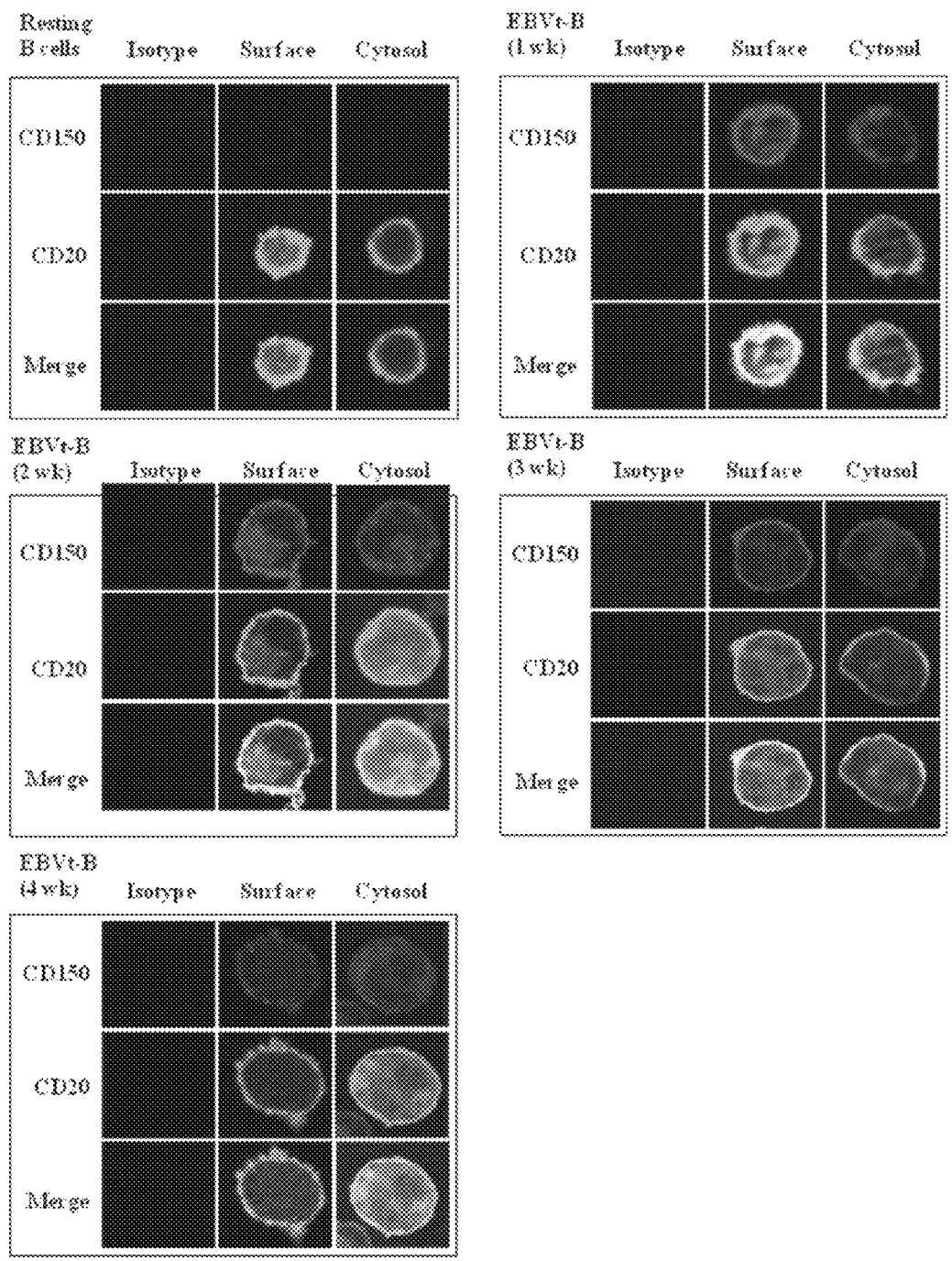
FIG. 2 shows confocal microscopic images showing expression of CD150 mRNA on B cells infected with EBV.

Similar results were observed at the mRNA level. Referring to FIG. 2, it was confirmed that CD150 mRNA was minimally expressed in resting B cells, but CD150 mRNA, which was weakly expressed until one week following infection, was highly expressed after 4 weeks of EBV infection.

<Example 2> Binding of CD150 Induces Production of Various Cytokines by EBV-Infected B Cells Cell proliferation after stimulation of CD150 on EBV-infected B cells was identified by using AlamarBlue (Serotec, Raleigh, N.C.) assay. Following stimulation of CD150 using both anti-CD150 mAb (IPO-3) and secondary Ab, acceleration of cell proliferation was identified. Subsequently, the inventors of the present invention examined whether the acceleration of cell proliferation was related to cytokine production since numerous cytokines are potent activators of cell survival. EBV-infected B cells were incubated with anti-CD150 mAb (IPO-3) or isotype control (UPC-10) and secondary Ab. After 24 h treatment with 1 μg/ml anti-CD150 mAb, a multiplex cytokine ELISA assay which enabled monitoring changes of multiple cytokines in culture supernatant from CD150-stimulated EBV-infected B cells.

Figure 3:
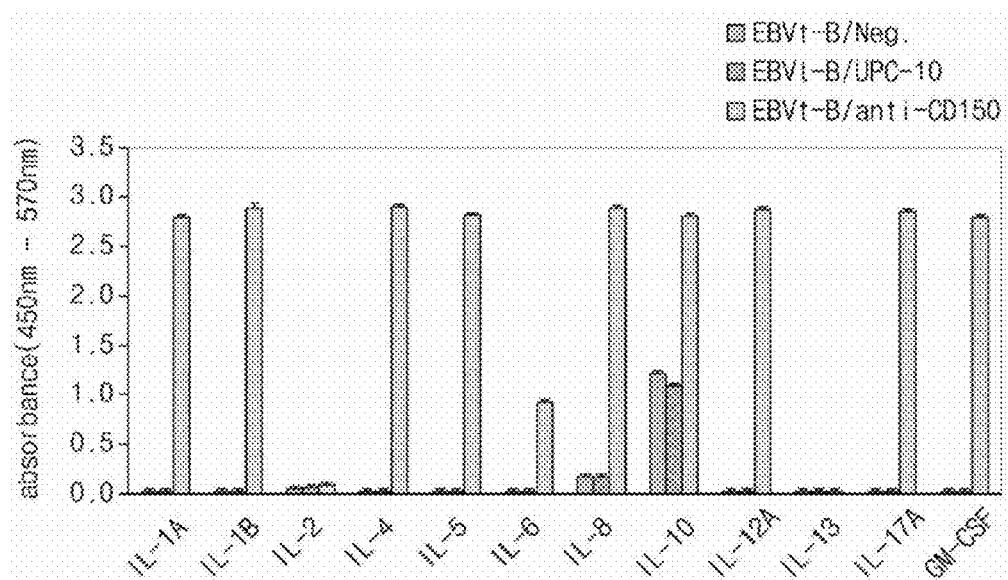
FIG. 3 shows ELISA experimental results on cytokines generated in EBV-infected B cells after the stimulation of CD150.
Figure 4:
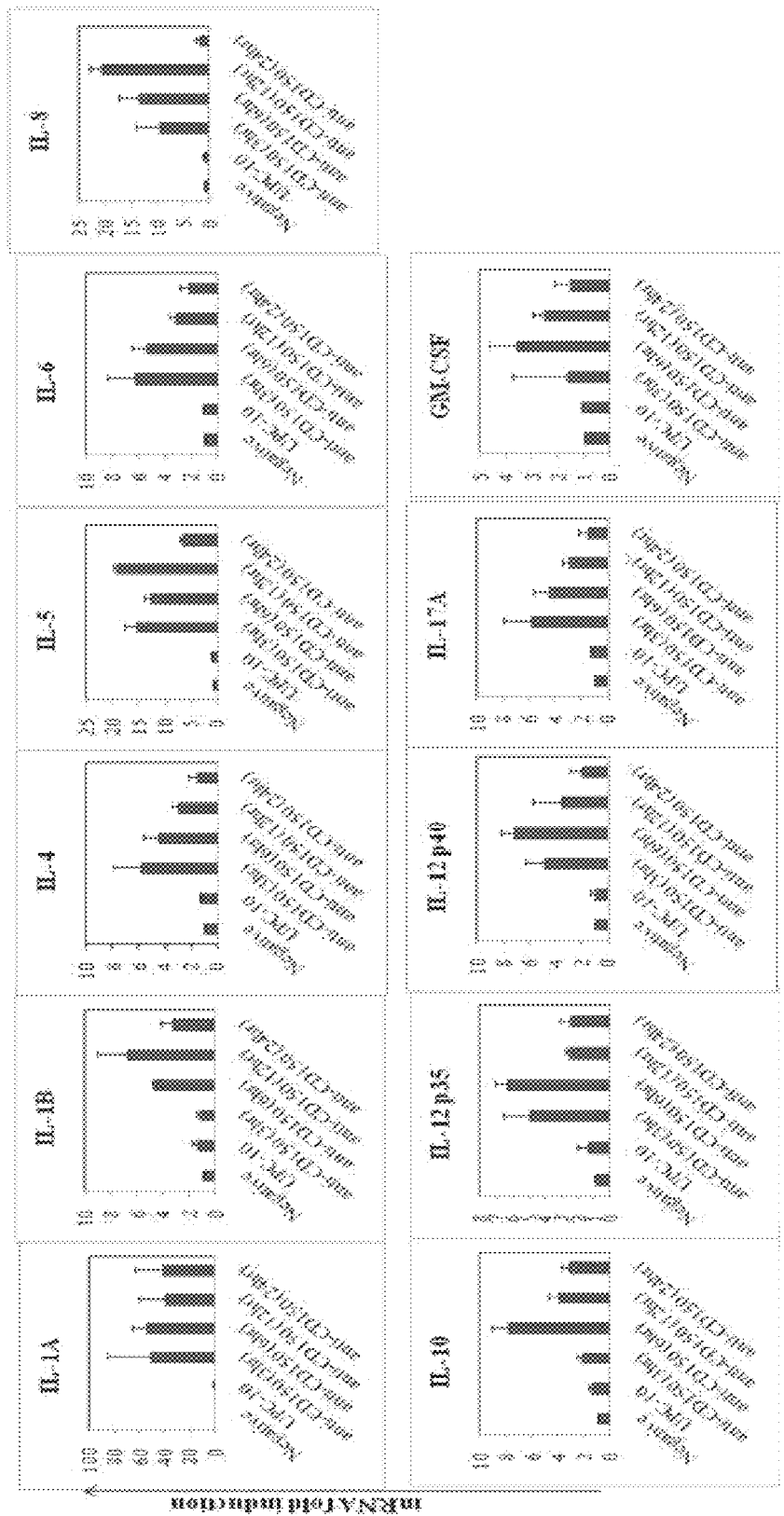
FIG. 4 shows quantitative real time RT-PCR results on mRNA expression of cytokines.
Figure 5:
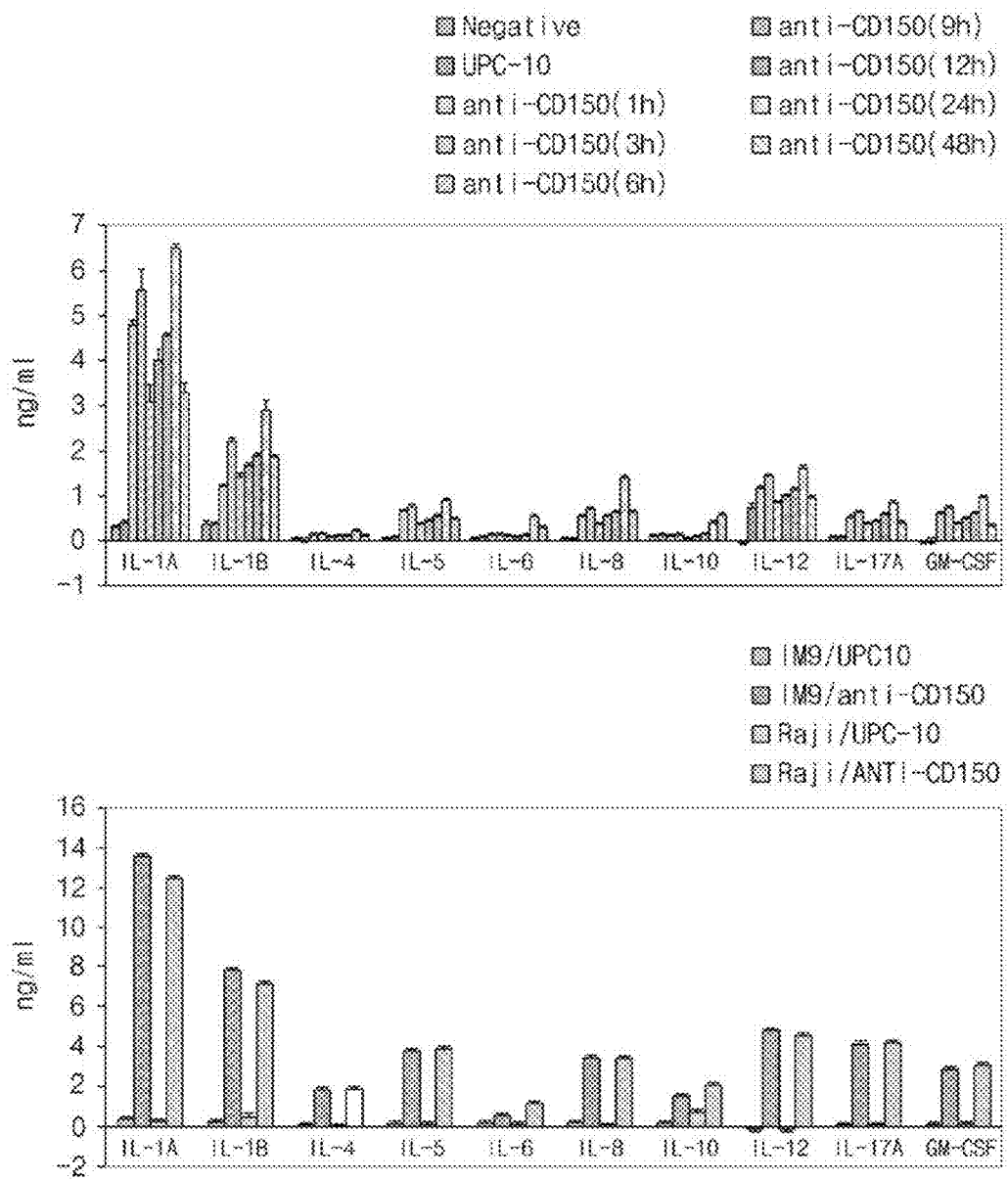
FIG. 5 shows ELISA analysis results of single cytokines.

Results are shown in FIG. 3. As shown in FIG. 3, after CD150 stimulation, cytokines other than IL-2 and IL-13 were measured, and negative and isotype control treated cells produced low levels of cytokines other than IL-10. To quantify the change in expression of these cytokine, quantitative real-time RT-PCR and single cytokine ELISA assay were performed for cytokines other than IL-2 and IL-13. Referring to FIGS. 4 and 5, it was confirmed that mRNA and protein levels with respect to all cytokines remarkably increased when CD150 was stimulated. In particular, the production of IL-1A following CD150 stimulation was remarkably high, with a maximum of 55-fold and 23-fold increase over that of other cytokines detected at mRNA and protein levels, respectively. To confirm these findings in other EBV-positive Burkitt's lymphoma cell lines and B lymphoblastoid cells, IM-9 and Raji cells were incubated with anti-CD150 mAb or isotype control and secondary Ab, and both of the cell lines, as shown in FIG. 5, showed increase in production of various cytokines following CD150 stimulation.

<Example 3> CD150 Knockdown on EBV-Infected B Cells Shows Decreased Capacity to Stimulate Cytokine Production Based on our data, the inventors of the present invention hypothesized that CD150 might have a positive role in the production of multiple cytokines. To definitively demonstrate that CD150 was responsible for regulating production of various cytokines, siRNA specific for CD150 was used. First, to determine the efficacy and specificity of three different siRNA (si-CD150 #1, #2, and #3) in silencing CD150 expression on EBV-infected B cells, the magnitude, off-target effects and duration of knockdown at mRNA and protein levels were studied. Non-target control siRNA was included in experiments as a negative control. EBV-infected B cells were electroporated with or without 200 nM siRNA and subsequently cultured in complete medium. After 24 h or 48 h, cells were collected to detect expression of CD150 mRNA by RT-PCR. Results are shown in FIG. 6.

Figure 6:
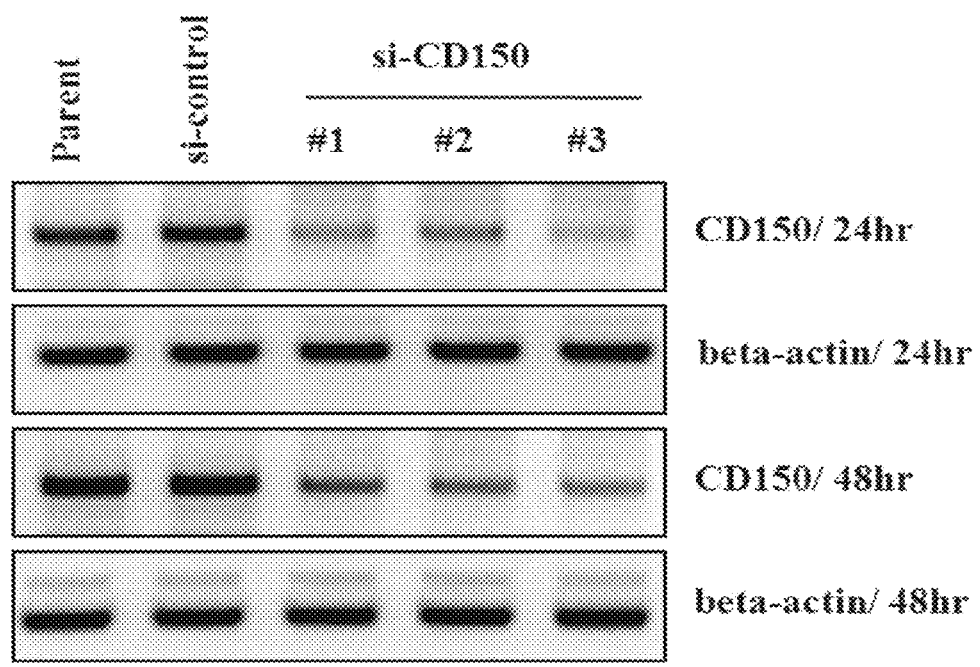
FIG. 6 shows images of CD150 mRNA expression results with respect to three kinds of CD150 siRNA.

Referring to FIG. 6, all three CD150 siRNAs reduced CD150 mRNA levels appreciably one or two days after electroporation while the negative control siRNAs had no effect.

Figure 7:
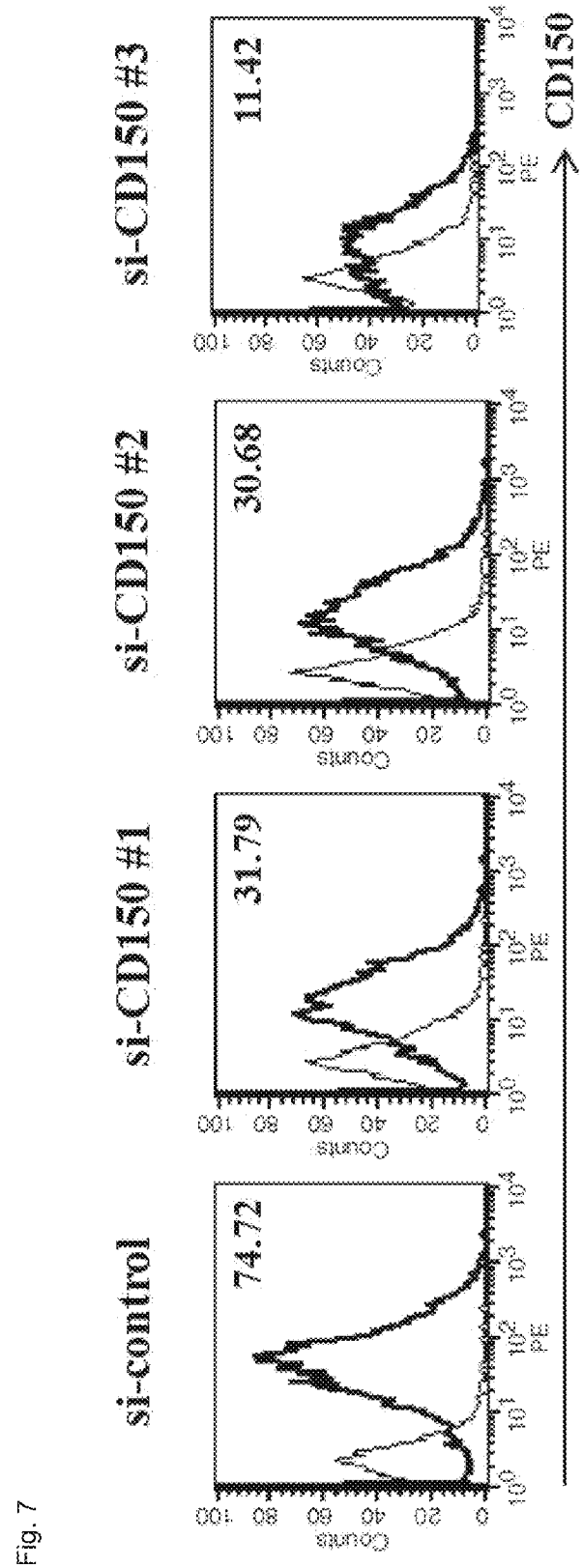
FIG. 7 shows CD150 protein expression results with respect to three kinds of CD150 siRNA.

To validate knockdown at the protein level, CD150 surface expression on siRNA-electroporated EBV-infected B cells two days after transfection was analyzed. CD150 siRNA number 3 induced the most pronounced reduction of CD150 cell surface expression, resulting in an average of 24.68% CD150$^+$ EBV-infected B cells (n=3, see FIG. 7). Therefore, CD150 siRNA number 3 and the accompanying GC negative control siRNA were continuously used in this experiment.

To investigate whether knockdown of CD150 using the selected siRNA number 3 diminished cytokine production via CD150 stimulation, EBV-infected B cells were incubated with anti-CD150 mAb or isotype control. After 24 h, the levels and kinetics of various cytokines produced by EBV-infected B cells with or without siRNA was analyzed using real-time PCR and ELISA. Results are shown in FIGS. 8 and 9.

Figure 8:
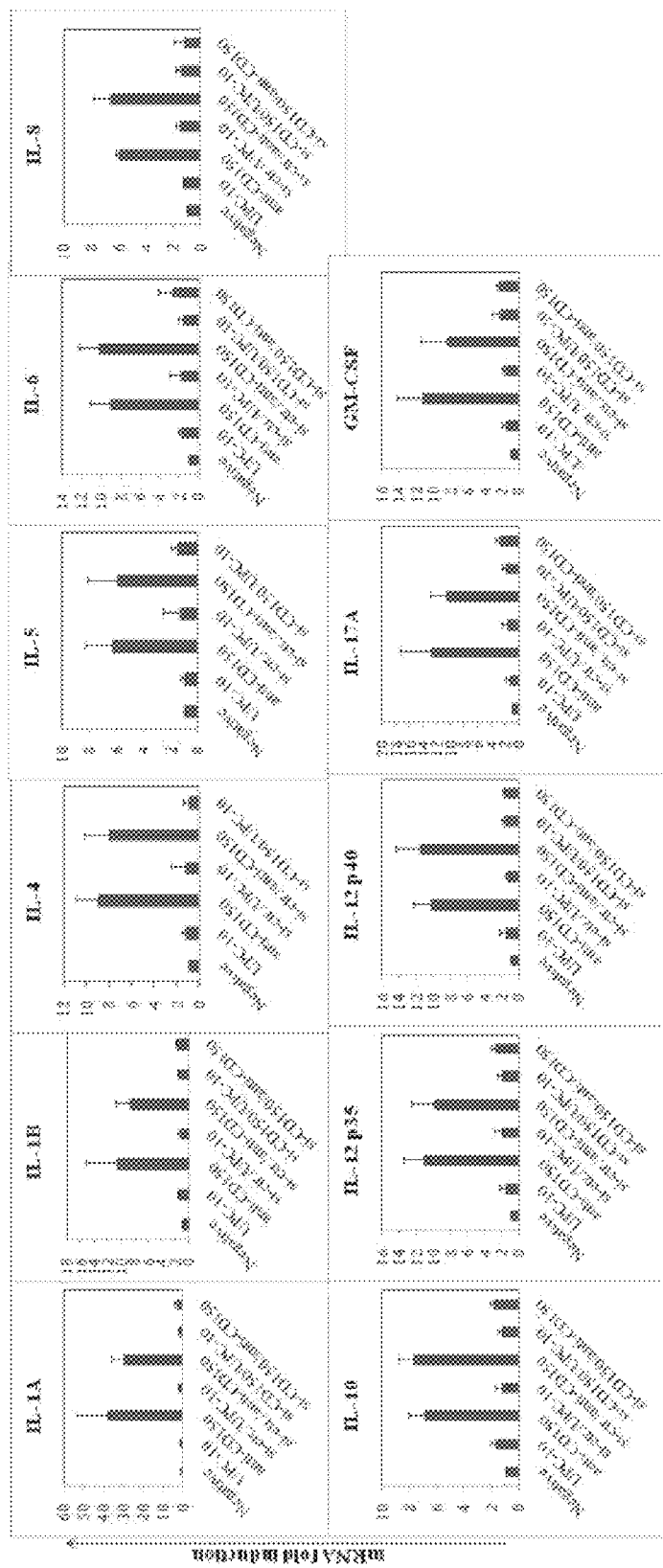
FIG. 8 shows real time PCR results on cytokines expression according to the treatment with CD150 siRNA.
Figure 9:
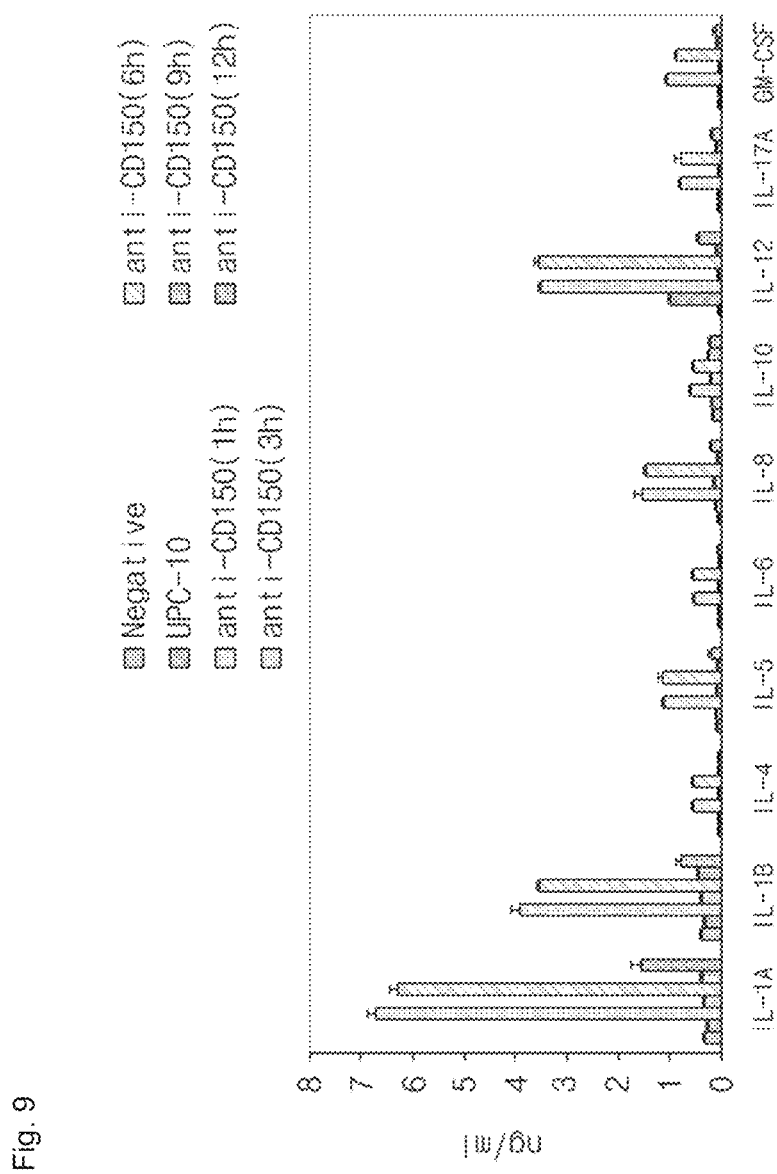
FIG. 9 shows ELISA analysis results on cytokines expression according to the treatment with CD150 siRNA.

Referring to FIGS. 8 and 9, it was confirmed that with CD150 suppression, stimulation of CD150 using anti-CD150 mAb did not induce transcription and translation of the cytokines measured. These observations imply that CD150 regulates production of multiple cytokines.

<Example 4> Cytokines Produced Following CD150 Stimulation Induce Differentiation of Monocytes into Dendritic Cells The inventors of the present invention examined the effect of multiple cytokines secreted following CD150 stimulation on differentiation of monocytes into dendritic cells (DCs). Monocytes were isolated from human PBMCs and were subsequently cultured with CD150-stimulated cell culture supernatant for 1 to 7 days to allow them to differentiate into DCs. The phenotypes of differentiated cells were ensured by detecting cell-type-specific surface markers, including CD1a, CD14, CD83, CD80, CD86, HLA-DR and CD11c, and morphology was determined by light microscopy. Results are shown in FIG. 10.

Figure 10:
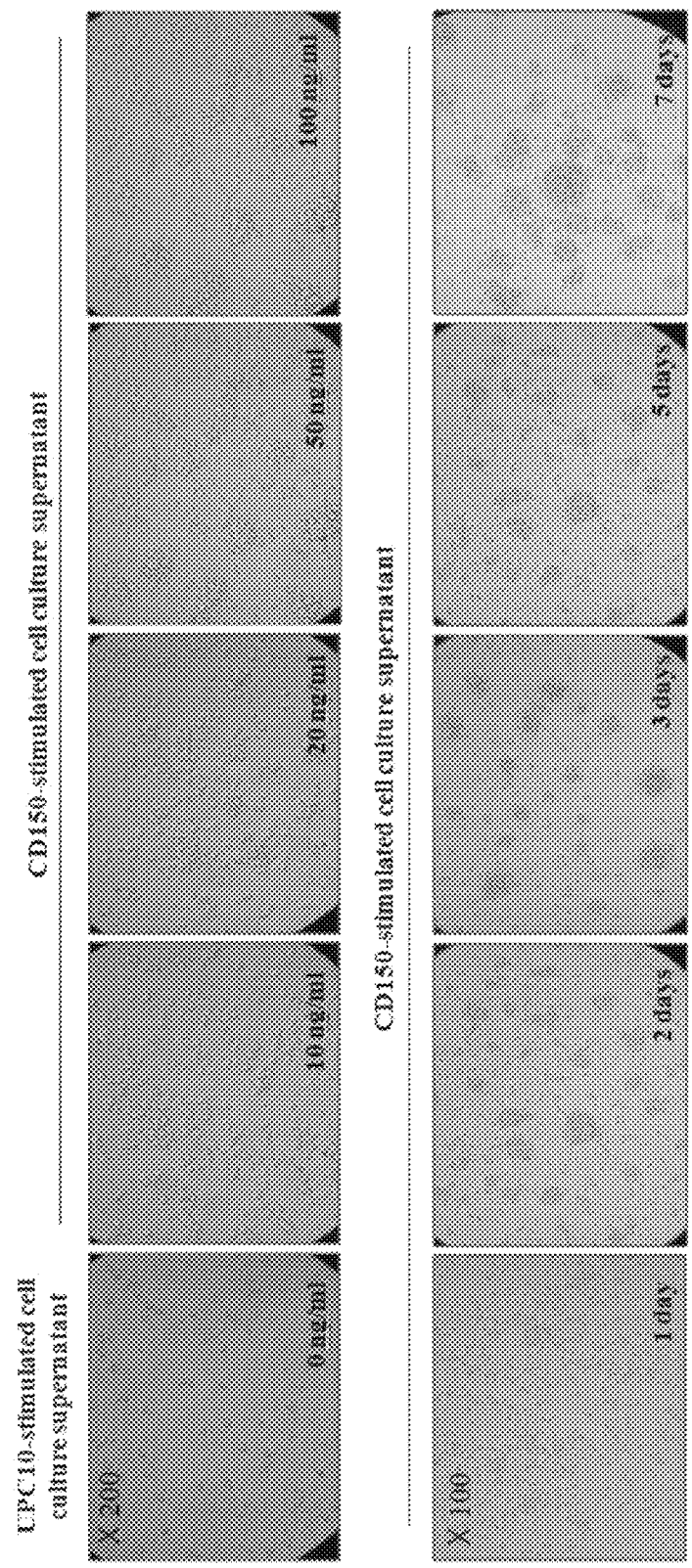
FIG. 10 shows a morphology image of dendritic cells produced by differentiation according to the cytokines treatment.

Referring to FIG. 10, exposure of normal monocytes to culture supernatant resulted in clustering and formation of cells with morphology typical of DCs within 2 days, and cells retained DC morphology for at least 7 days.

Figure 11:
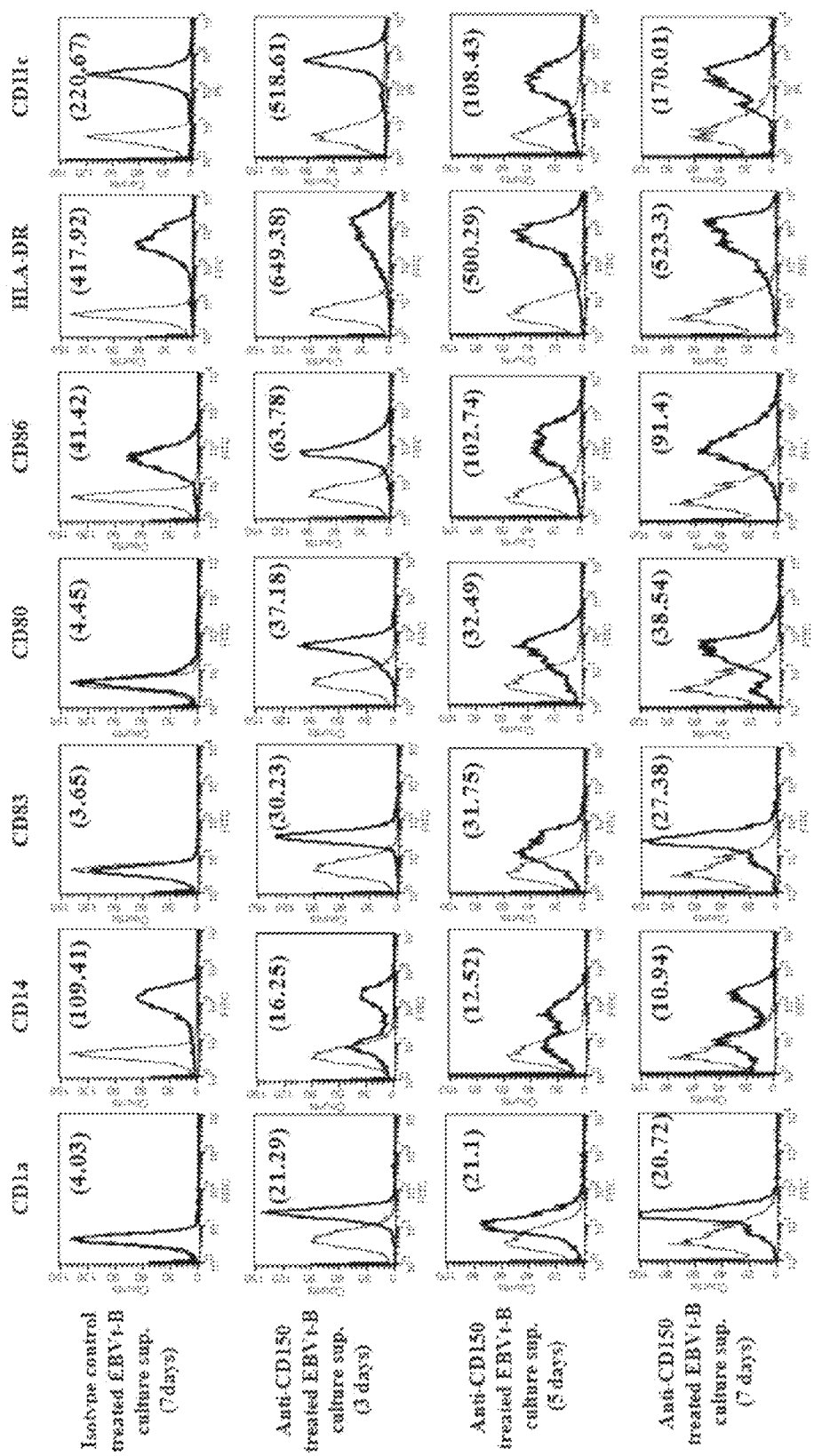
FIG. 11 shows flow cytometric results on immunophenotype of monocytes differentiated into dendritic cells (DCs).
Figure 12:
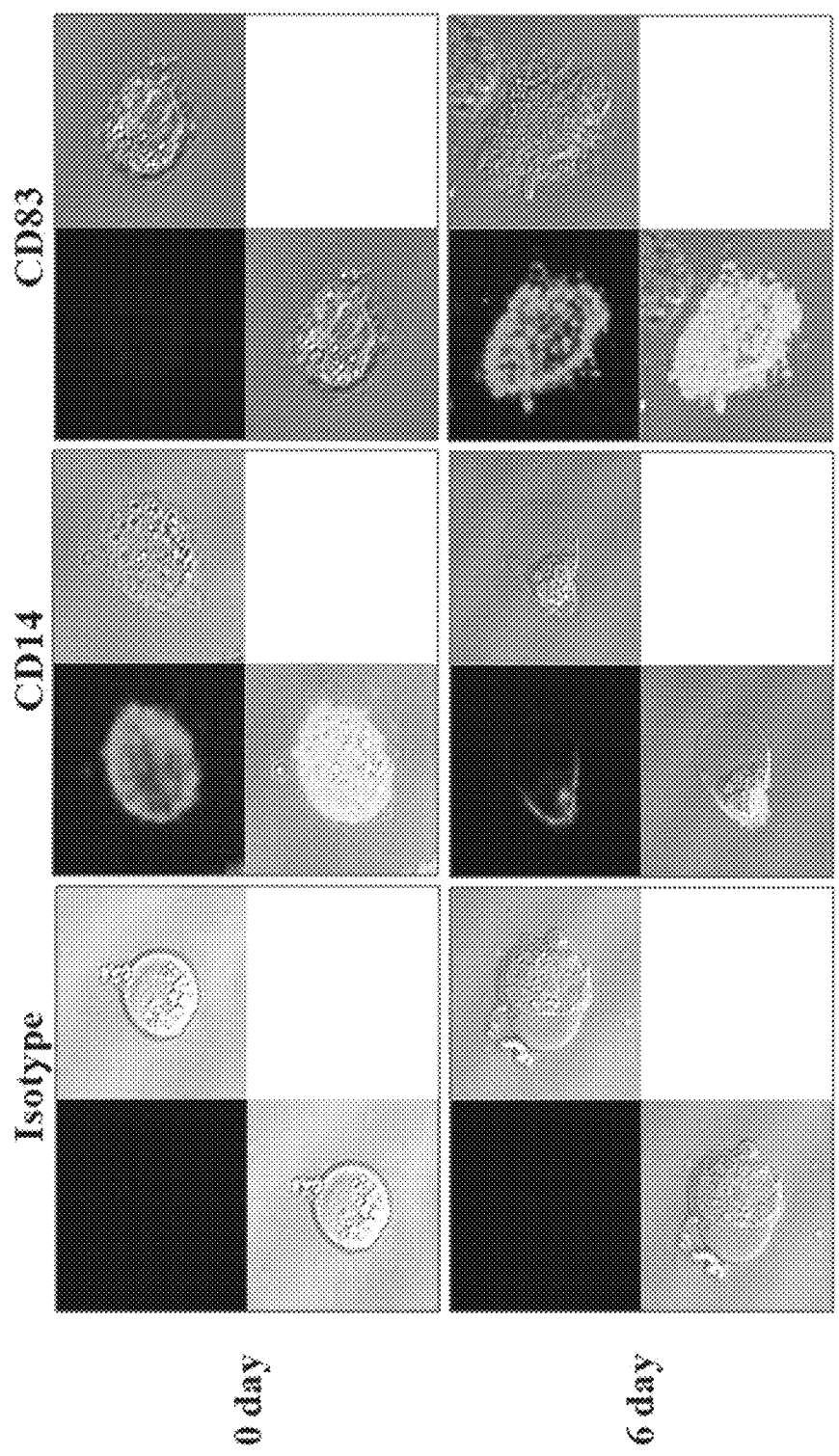
FIG. 12 shows confocal microscopic images of monocytes differentiated into DC according to immunophenotype.

The inventors of the present invention compared basic phenotypic and functional qualities of monocytes and CD150-induced cytokine-mediated mature DCs. Monocytes expressed virtually no detectable CD83, CD1a, or CD80 and retained relatively moderate levels of CD14, CD86, HLA-DR, and CD11c. In contrast, monocytes incubated with CD150-stimulated cell culture supernatant for 7 days developed into mature DCs that expressed elevated levels of CD83, CD80, and CD1a as well as depressed levels of CD14 consistent with mature DC development. Interestingly, these cells displayed a pattern of surface markers consistent with fully mature DC immunophenotype (CD83+CD40+CD14-CD80+CD86highMHC-IIhigh) after only 2 days in culture, and the duration of development into mature DCs was very short (2 days) compared with general DC maturation duration (5 to 7 days) (see FIGS. 11 and 12).

Rapid DC maturation from monocytes can also be induced by adding pro-inflammatory mediators together with GM-CSF and IL-4 at the initiation of culture. Therefore, these results point to CD150 as a major molecule mediating production of various cytokine in B cells.

<Example 5> Stimulation by CD150 Ligands, Measles Virus or Recombinant CD150 Protein, Induces Production of Multiple Cytokines Many viruses use cell surface glycoproteins, which possess immunoglobulin (Ig) superfamily domains or complement control protein domains, also called short consensus repeats (SLRs), as receptors. These viruses include EBV (binds CD21), HIV (binds CD4), rhinoviruses (binds CD54), poliovirus (binds CD155), enterovirus 70 and coxsackie virus (both bind CD55), and MV (binds CD150 and CD46). Therefore, CD150 acts as a receptor for MV and mediates virus uptake. Therefore, the inventors of the present invention tested whether MV core protein treatment induced production of various cytokine in a manner similar to anti-CD150 mAb treatment. EBV-infected B cells, Raji cells, and IM-9 cells were incubated with MV#1 (1 μg/ml) or MV#2 (1 μg/ml) for 24 h. Then, cell culture supernatants were collected, concentrated, and secreted cytokine levels were measured using a multiple cytokine ELISA assay kit.

Figures 13, 14:
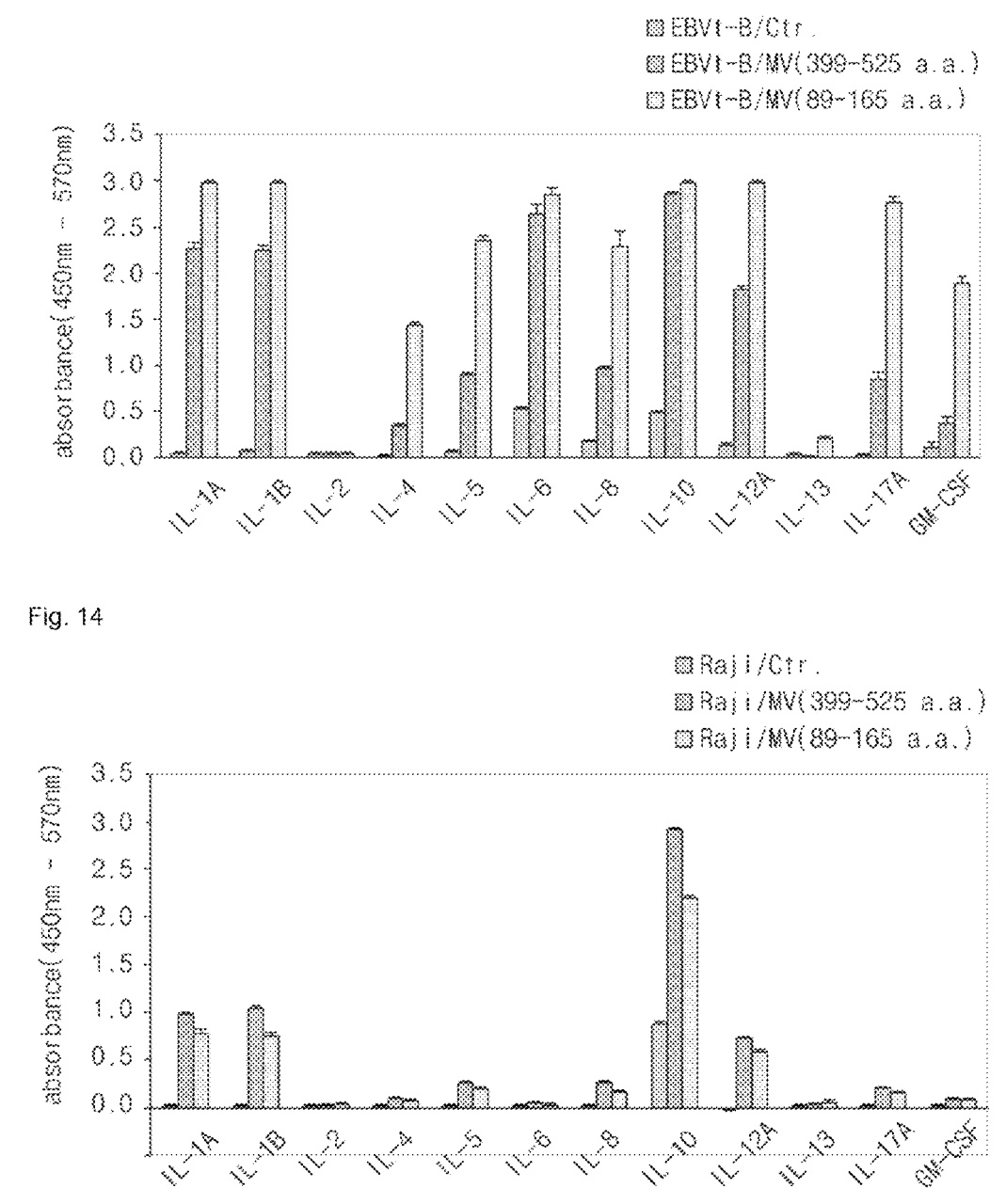
Figure 15:
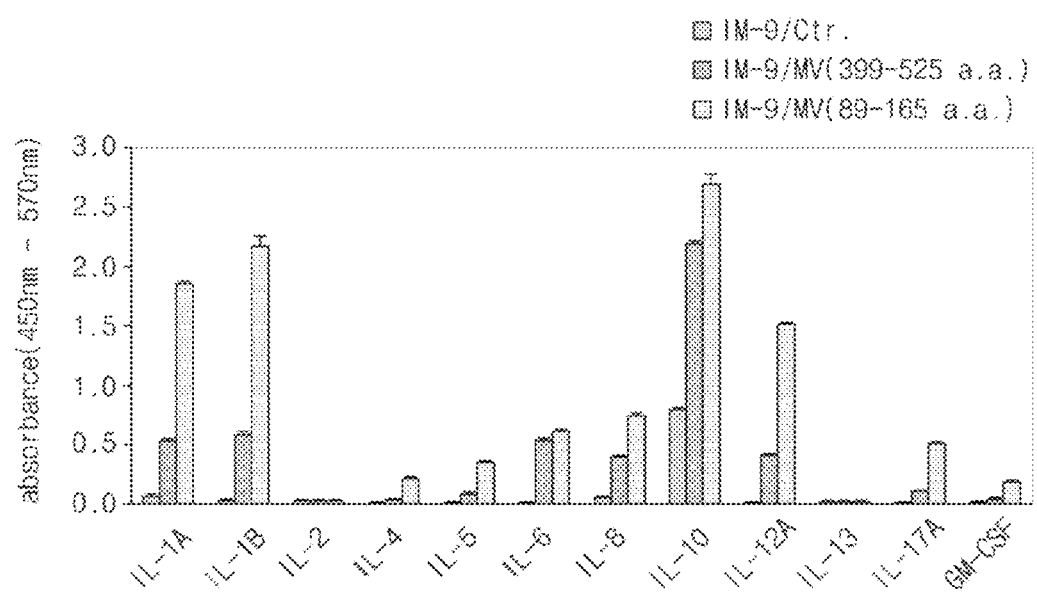
FIG. 15 shows ELISA analysis results on cytokines generated according to CD150 stimulating molecules, in IM-9 cells.

Results are shown in FIGS. 13 to 15.

Referring to FIG. 13, in EBV-infected B cells, MV#1 and MV#2 stimulated production of most cytokines measured, with the exception of IL-2, which was not detected, and IL-13, which was only slightly increased following stimulation with MV#2.

Referring to FIG. 14, in Raji cells, IL-1A, IL-1B, IL-10, and IL-12A were remarkably increased, while IL-5, IL-8, and IL-17A secretion levels were slightly increased. The remaining cytokines measured were not detected.

Referring to FIG. 15, in IM-9 cells, IL-1A, IL-1B, IL-10, and IL-12A were prominently elevated, IL-5, IL-6, IL-8, and IL-17A were moderately elevated, and IL-4 and GM-CSF levels were slightly elevated. IL-2 and IL-13 were not detected. IL-2 and IL-13 were not detected.

Figure 16:
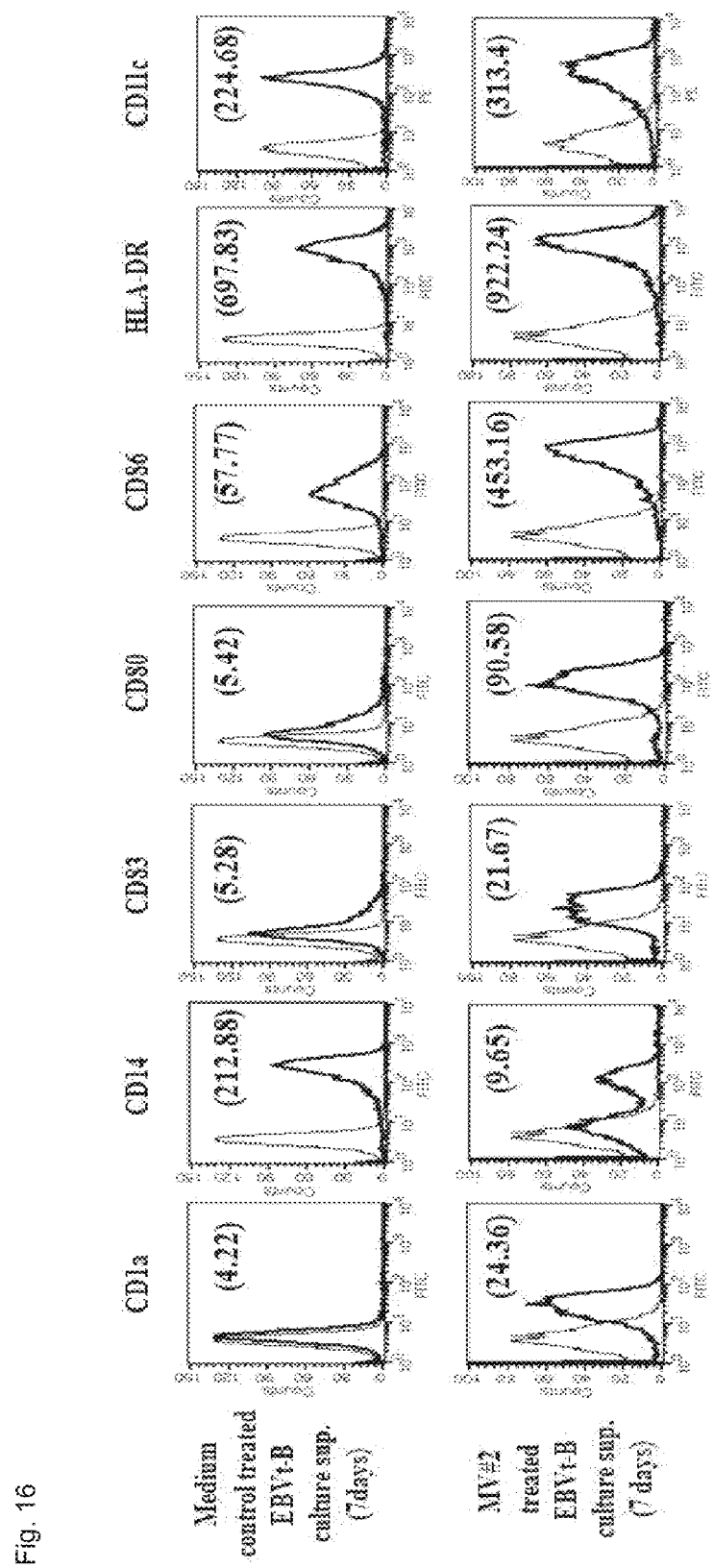
FIG. 16 shows flow cytometric results on phenotype of differentiated cells.
Figure 17:
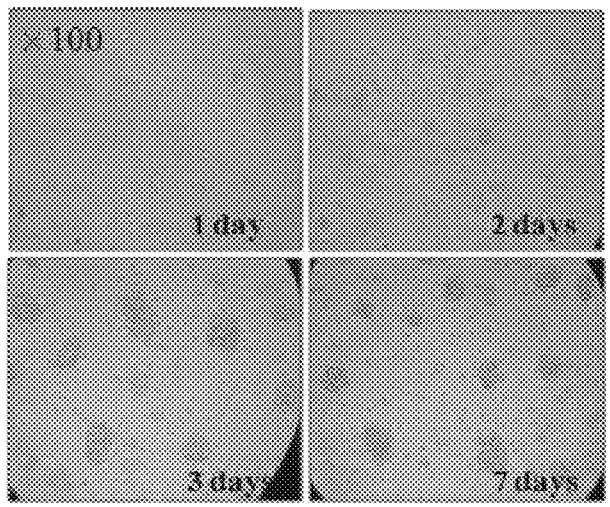
FIG. 17 shows optical microscopic images of differentiated cells according to phenotype.

The phenotypes and morphology of differentiated cells were determined by flow cytometry and light microscopy, respectively. Results are shown in FIGS. 16 and 17. Monocytes cultured in normal medium did not form clustering or express CD83, CD1a, and CD80. Meanwhile, cells that differentiated into DCs showed decreased CD14 and high CD83 and CD1a expression, consistent with mature DC development. Moreover, these cells displayed higher levels of CD80, CD86, and MHC-II expression and prominently formed clustering (see FIG. 17).

Figure 18:
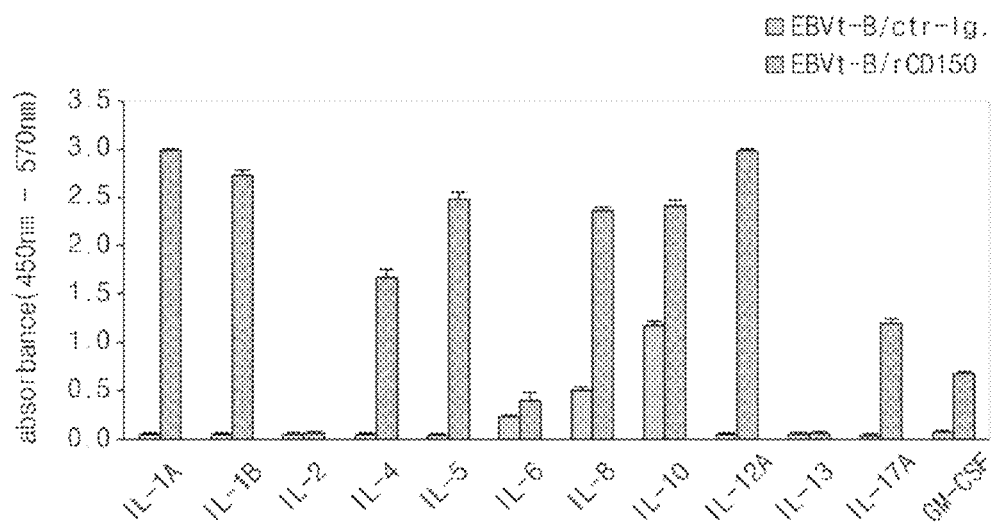
FIG. 18 show ELISA analysis results on cytokines generated in EBV-infected B cells according to the treatment with recombinant CD150 fusion protein used as a CD150 stimulation molecule.

Referring to FIG. 18, when EBV-infected B cells were stimulated with recombinant CD150 fusion protein (1 μg/ml, 24 h) as a natural ligand of CD150, cytokine production induced by anti-CD150 mAb was repeatedly performed.

<Example 6> Fyn/Lyn and PI3K/AKT Pathways are Involved in CD150 Signaling

Although the involvement of CD150 in regulating a variety of cellular functions, including the regulation of proliferation and production of mitogen and some cytokines, has been described in considerable detail, the ability of CD150 to regulate the production of multiple inflammatory cytokines has not been demonstrated. Accordingly, the inventors of the present invention investigated the regulatory signaling mechanisms leading to CD150-induced cytokine production.

It has been reported that signaling of the CD150-mediated Akt activation in DT40 model system and Hodgkin's lymphoma cell lines is initiated via Akt activation and could be regulated by SAP expression. Therefore, whether this system is related to the induction of multiple cytokines in EBV-infected B cells treated with anti-CD150 mAb was confirmed.

Figure 19:
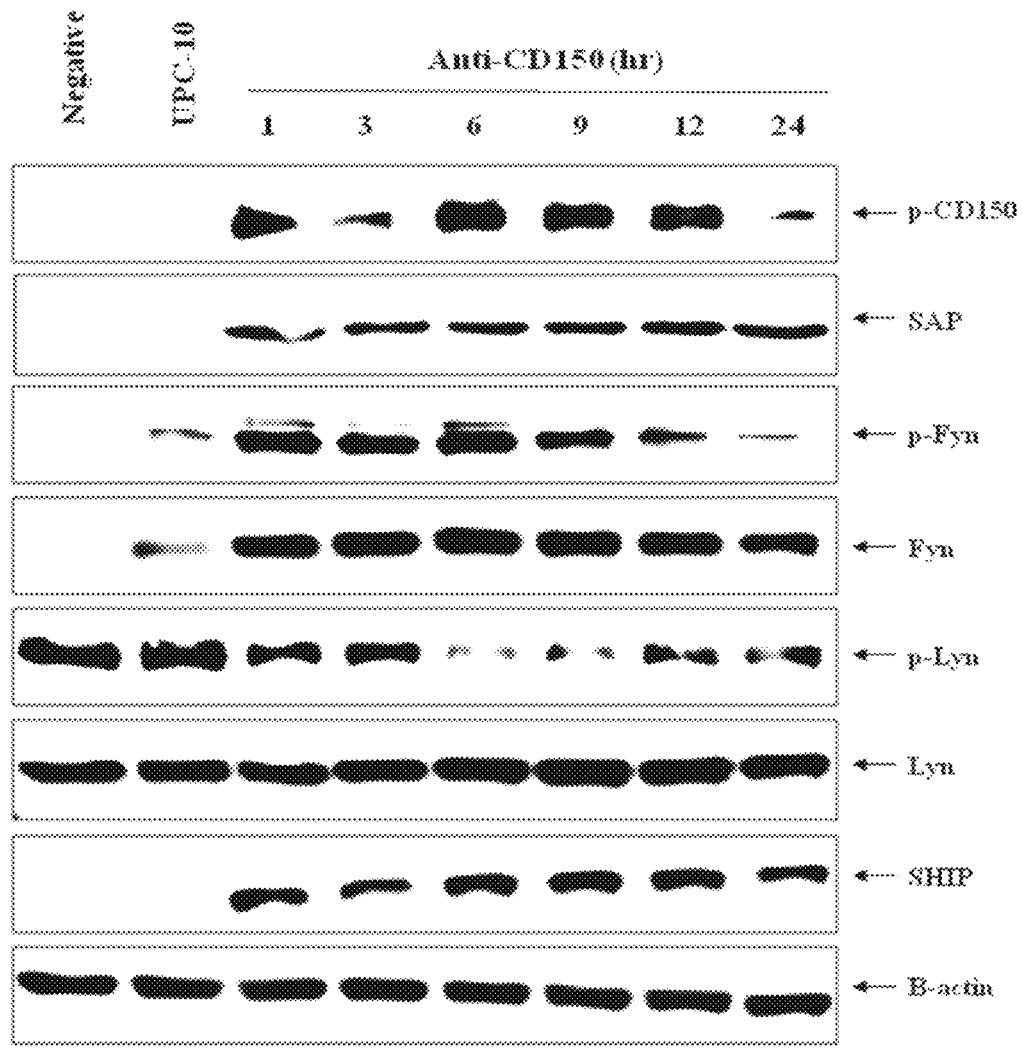
FIGS. 19 and 20 show western blotting results regarding intracellular signaling molecules.
Figure 20:
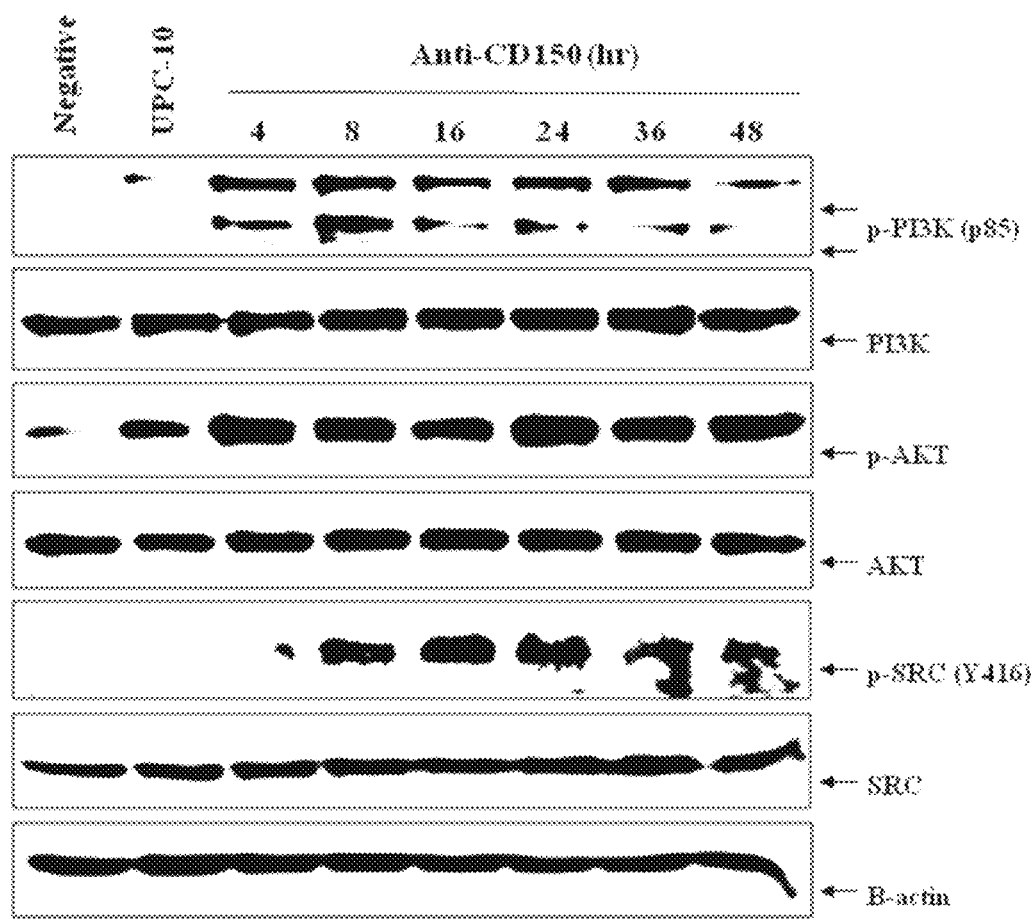
Figure 21:
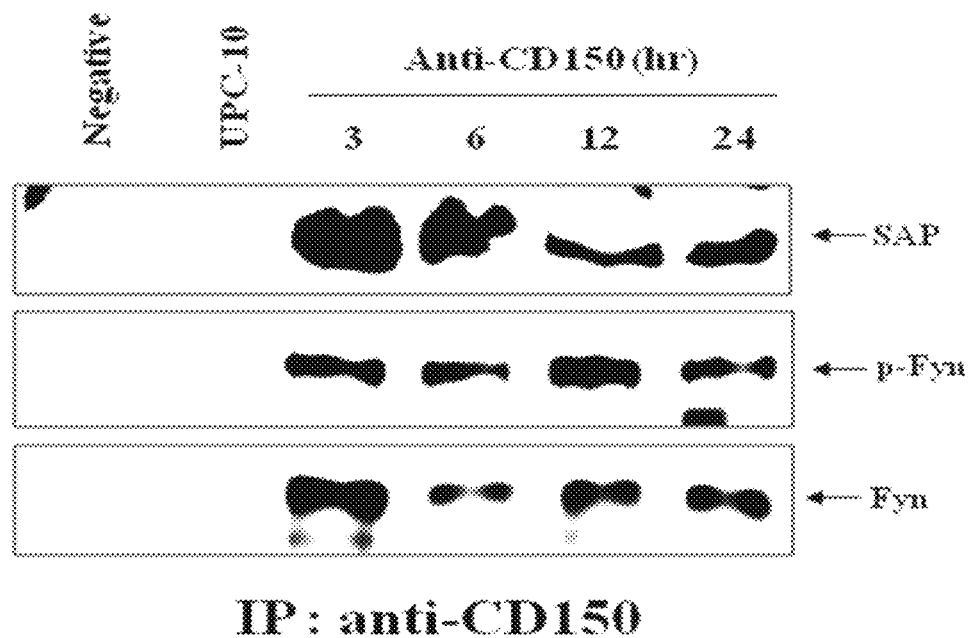
FIG. 21 shows immunoprecipitation test results regarding intracellular signaling molecules.

To assess whether CD150-induced cytokine production involved these signaling pathways, associated signals were detected using western blot analysis and immunoprecipitation. Results are shown in FIGS. 19 to 21. FIGS. 19 and 29 show experimental results of western blotting, and FIG. 21 show experimental results of immunoprecipitation.

Referring to FIGS. 19 to 21, it was confirmed that CD150 was phosphorylated 1 to 24 h after CD150 stimulation, and Fyn was phosphorylated. Additionally, PI3K/Atk and SRC were phosphorylated. To confirm that signaling via CD150 is initiated by recruitment of SAP and Fyn to CD150, co-IP was performed. (see FIG. 21) Lysates from CD150-stimulated EBV-infected B cells were immunoprecipitated using anti-CD150 mAb and immunoblotting was performed using anti-SAP and -Fyn Abs. As a result, it was confirmed that the CD150 receptor is able to trigger PI3K-mediated Akt signaling pathway in EBV-infected B cells.

It should be understood that the exemplary embodiments described herein should be considered in a descriptive sense only and not for purposes of limitation. Descriptions of features or aspects within each embodiment should typically be considered as available for other similar features or aspects in other embodiments.

The invention claimed is:

1. A method of producing dendritic cells, the method comprising:

a) isolating monocytes from human peripheral blood mononuclear cells (PBMCs);

b) generating a culture supernatant consisting essentially of cytokines interleukin-1 A, interleukin-1B, interleukin-4, interleukin-5, interleukin-6, interleukin-8, interleukin-10, interleukin-12, interleukin-17A, and Granulocyte-macrophage colony-stimulating factor (GM-CSF);

wherein the culture supernatant is generated by:

(i) incubating Epstein-Barr virus (EBV)-infected B cells with an anti-CD150 antibody to stimulate CD150 expressed on the surface of the EBV-infected B cells; or (ii) incubating Epstein-Barr virus (EBV)-infected B cells with a measles virus core protein selected from the group consisting of MV1 (SEQ ID NO: 34) and MV2 (SEQ ID NO: 35) to stimulate CD150 expressed on the surface of the EBV-infected B cells;

wherein the stimulation of CD150 on the surface of the EBV-infected B cells induces the secretion of interleukin-1 A, interleukin-1B, interleukin-4, interleukin-5, interleukin-6, interleukin-8, interleukin-10, interleukin-12, interleukin-17A, and Granulocyte-macrophage colony-stimulating factor (GM-CSF) into the supernatant; and c) differentiating the monocytes into dendritic cells by culturing the monocytes with the supernatant obtained from step b) above to produce the dendritic cells.

* * * * *

SEQUENCE LISTING

<160> NUMBER OF SEQ ID NOS: 35

<210> SEQ ID NO 1
<211> LENGTH: 22
<212> TYPE: DNA
<213> ORGANISM: Artificial Sequence
<220> FEATURE:
<223> OTHER INFORMATION: Synthetic Primer

<400> SEQUENCE: 1
tatctacatc tgcaccgtga gc                                            22

<210> SEQ ID NO 2
<211> LENGTH: 19
<212> TYPE: DNA
<213> ORGANISM: Artificial Sequence
<220> FEATURE:
<223> OTHER INFORMATION: Synthetic Primer

<400> SEQUENCE: 2
tcctgagctg ggaaggagt                                                19

<210> SEQ ID NO 3
<211> LENGTH: 18
<212> TYPE: DNA
<213> ORGANISM: Artificial Sequence
<220> FEATURE:
<223> OTHER INFORMATION: Synthetic Primer

```
<400> SEQUENCE: 3
ctgcatggat caatctgt                                                 18

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
cccatgtcaa atttcactgc                                               20

<210> SEQ ID NO 5
<211> LENGTH: 21
<212> TYPE: DNA
<213> ORGANISM: Artificial Sequence
<220> FEATURE:
<223> OTHER INFORMATION: Synthetic Primer

<400> SEQUENCE: 5
cagctacgaa tctccgacca c                                             21

<210> SEQ ID NO 6
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
ggcagggaac cagcatcttc                                               20

<210> SEQ ID NO 7
<211> LENGTH: 24
<212> TYPE: DNA
<213> ORGANISM: Artificial Sequence
<220> FEATURE:
<223> OTHER INFORMATION: Synthetic Primer

<400> SEQUENCE: 7
atgggtctca cctcccaact gctt                                          24

<210> SEQ ID NO 8
<211> LENGTH: 22
<212> TYPE: DNA
<213> ORGANISM: Artificial Sequence
<220> FEATURE:
<223> OTHER INFORMATION: Synthetic Primer

<400> SEQUENCE: 8
tttccaacgt actctggttg gc                                            22

<210> SEQ ID NO 9
<211> LENGTH: 20
<212> TYPE: DNA
<213> ORGANISM: Artificial Sequence
<220> FEATURE:
<223> OTHER INFORMATION: Synthetic Primer

<400> SEQUENCE: 9
tctgaggatt cctgttcctg                                               20

<210> SEQ ID NO 10
<211> LENGTH: 20
```

```
<212> TYPE: DNA
<213> ORGANISM: Artificial Sequence
<220> FEATURE:
<223> OTHER INFORMATION: Synthetic Primer

<400> SEQUENCE: 10
ttatccactc ggtgttcatt                                            20

<210> SEQ ID NO 11
<211> LENGTH: 22
<212> TYPE: DNA
<213> ORGANISM: Artificial Sequence
<220> FEATURE:
<223> OTHER INFORMATION: Synthetic Primer

<400> SEQUENCE: 11
gtgttgcctg ctgccttccc tg                                         22

<210> SEQ ID NO 12
<211> LENGTH: 24
<212> TYPE: DNA
<213> ORGANISM: Artificial Sequence
<220> FEATURE:
<223> OTHER INFORMATION: Synthetic Primer

<400> SEQUENCE: 12
ctctaggtat acctcaaact ccaa                                       24

<210> SEQ ID NO 13
<211> LENGTH: 24
<212> TYPE: DNA
<213> ORGANISM: Artificial Sequence
<220> FEATURE:
<223> OTHER INFORMATION: Synthetic Primer

<400> SEQUENCE: 13
atgacttcca agctggccgt ggct                                       24

<210> SEQ ID NO 14
<211> LENGTH: 25
<212> TYPE: DNA
<213> ORGANISM: Artificial Sequence
<220> FEATURE:
<223> OTHER INFORMATION: Synthetic Primer

<400> SEQUENCE: 14
tctcagccct cttcaaaaac ttctc                                      25

<210> SEQ ID NO 15
<211> LENGTH: 27
<212> TYPE: DNA
<213> ORGANISM: Artificial Sequence
<220> FEATURE:
<223> OTHER INFORMATION: Synthetic Primer

<400> SEQUENCE: 15
ctgagaacca agacccagac atcaagg                                    27

<210> SEQ ID NO 16
<211> LENGTH: 27
<212> TYPE: DNA
<213> ORGANISM: Artificial Sequence
<220> FEATURE:
<223> OTHER INFORMATION: Synthetic Primer

<400> SEQUENCE: 16
```
gtcagctatc ccagagcccc agatccg                                       27

<210> SEQ ID NO 17
<211> LENGTH: 21
<212> TYPE: DNA
<213> ORGANISM: Artificial Sequence
<220> FEATURE:
<223> OTHER INFORMATION: Synthetic Primer

<400> SEQUENCE: 17
cttcaccact cccaaaacct g                                             21

<210> SEQ ID NO 18
<211> LENGTH: 21
<212> TYPE: DNA
<213> ORGANISM: Artificial Sequence
<220> FEATURE:
<223> OTHER INFORMATION: Synthetic Primer

<400> SEQUENCE: 18
agctcatcac tctatcaata g                                             21

<210> SEQ ID NO 19
<211> LENGTH: 21
<212> TYPE: DNA
<213> ORGANISM: Artificial Sequence
<220> FEATURE:
<223> OTHER INFORMATION: Synthetic Primer

<400> SEQUENCE: 19
cattcgctcc tgctgcttca c                                             21

<210> SEQ ID NO 20
<211> LENGTH: 21
<212> TYPE: DNA
<213> ORGANISM: Artificial Sequence
<220> FEATURE:
<223> OTHER INFORMATION: Synthetic Primer

<400> SEQUENCE: 20
tactccttgt tgtcccctct g                                             21

<210> SEQ ID NO 21
<211> LENGTH: 24
<212> TYPE: DNA
<213> ORGANISM: Artificial Sequence
<220> FEATURE:
<223> OTHER INFORMATION: Synthetic Primer

<400> SEQUENCE: 21
atgactcctg ggaagacctc attg                                          24

<210> SEQ ID NO 22
<211> LENGTH: 24
<212> TYPE: DNA
<213> ORGANISM: Artificial Sequence
<220> FEATURE:
<223> OTHER INFORMATION: Synthetic Primer

<400> SEQUENCE: 22
ttaggccaca tggtggacaa tcgg                                          24

<210> SEQ ID NO 23
<211> LENGTH: 22
<212> TYPE: DNA
<213> ORGANISM: Artificial Sequence

```
<220> FEATURE:
<223> OTHER INFORMATION: Synthetic Primer

<400> SEQUENCE: 23
atgtggctgc agagcctgct gc                                              22

<210> SEQ ID NO 24
<211> LENGTH: 22
<212> TYPE: DNA
<213> ORGANISM: Artificial Sequence
<220> FEATURE:
<223> OTHER INFORMATION: Synthetic Primer

<400> SEQUENCE: 24
ctggctccca gcagtcaaag gg                                              22

<210> SEQ ID NO 25
<211> LENGTH: 20
<212> TYPE: DNA
<213> ORGANISM: Artificial Sequence
<220> FEATURE:
<223> OTHER INFORMATION: Synthetic Primer

<400> SEQUENCE: 25
atccacgaaa ctaccttcaa                                                 20

<210> SEQ ID NO 26
<211> LENGTH: 19
<212> TYPE: DNA
<213> ORGANISM: Artificial Sequence
<220> FEATURE:
<223> OTHER INFORMATION: Synthetic Primer

<400> SEQUENCE: 26
atccacacgg agtacttgc                                                  19

<210> SEQ ID NO 27
<211> LENGTH: 19
<212> TYPE: RNA
<213> ORGANISM: Artificial Sequence
<220> FEATURE:
<223> OTHER INFORMATION: Synthetic Primer

<400> SEQUENCE: 27
gugucaucau gauucucau                                                  19

<210> SEQ ID NO 28
<211> LENGTH: 19
<212> TYPE: RNA
<213> ORGANISM: Artificial Sequence
<220> FEATURE:
<223> OTHER INFORMATION: Synthetic Primer

<400> SEQUENCE: 28
augagaauca ugaugacac                                                  19

<210> SEQ ID NO 29
<211> LENGTH: 19
<212> TYPE: RNA
<213> ORGANISM: Artificial Sequence
<220> FEATURE:
<223> OTHER INFORMATION: Synthetic Primer

<400> SEQUENCE: 29
gguaccuuau gacccugga                                                  19
```

<210> SEQ ID NO 30
<211> LENGTH: 19
<212> TYPE: RNA
<213> ORGANISM: Artificial Sequence
<220> FEATURE:
<223> OTHER INFORMATION: Synthetic Primer

<400> SEQUENCE: 30
uccaggguca uaagguacc 19

<210> SEQ ID NO 31
<211> LENGTH: 19
<212> TYPE: RNA
<213> ORGANISM: Artificial Sequence
<220> FEATURE:
<223> OTHER INFORMATION: Synthetic Primer

<400> SEQUENCE: 31
gagaucgcua caaguuuua 19

<210> SEQ ID NO 32
<211> LENGTH: 19
<212> TYPE: RNA
<213> ORGANISM: Artificial Sequence
<220> FEATURE:
<223> OTHER INFORMATION: Synthetic Primer

<400> SEQUENCE: 32
uaaaacuugu agcgaucuc 19

<210> SEQ ID NO 33
<211> LENGTH: 525
<212> TYPE: PRT
<213> ORGANISM: Measles virus

<400> SEQUENCE: 33

```
Met Ala Thr Leu Leu Arg Ser Leu Ala Leu Phe Lys Arg Asn Lys Asp
1               5                   10                  15

Lys Pro Pro Ile Thr Ser Gly Ser Gly Gly Ala Ile Arg Gly Ile Lys
            20                  25                  30

His Ile Ile Ile Val Pro Ile Pro Gly Asp Ser Ser Ile Thr Thr Arg
        35                  40                  45

Ser Arg Leu Leu Asp Arg Leu Val Arg Leu Ile Gly Asn Pro Asp Val
    50                  55                  60

Ser Gly Pro Lys Leu Thr Gly Ala Leu Ile Gly Ile Leu Ser Leu Phe
65                  70                  75                  80

Val Glu Ser Pro Gly Gln Leu Ile Gln Arg Ile Thr Asp Asp Pro Asp
                85                  90                  95

Val Ser Ile Arg Leu Leu Glu Val Val Gln Ser Asp Gln Ser Gln Ser
            100                 105                 110

Gly Leu Thr Phe Ala Ser Arg Gly Thr Asn Met Glu Asp Glu Ala Asp
        115                 120                 125

Gln Tyr Phe Ser His Asp Asp Pro Ser Ser Ser Asp Gln Ser Arg Ser
    130                 135                 140

Gly Trp Phe Glu Asn Lys Glu Ile Ser Asp Ile Glu Val Gln Asp Pro
145                 150                 155                 160

Glu Gly Phe Asn Met Ile Leu Gly Thr Ile Leu Ala Gln Ile Trp Val
                165                 170                 175

Leu Leu Ala Lys Ala Val Thr Ala Pro Asp Thr Ala Ala Asp Ser Glu
            180                 185                 190
```

Leu Arg Arg Trp Ile Lys Tyr Thr Gln Gln Arg Arg Val Val Gly Glu
            195                 200                 205

Phe Arg Leu Glu Arg Lys Trp Leu Asp Val Val Arg Asn Arg Ile Ala
            210                 215                 220

Glu Asp Leu Ser Leu Arg Arg Phe Met Val Ala Leu Ile Leu Asp Ile
225                 230                 235                 240

Lys Arg Thr Pro Gly Asn Lys Pro Arg Ile Ala Glu Met Ile Cys Asp
            245                 250                 255

Ile Asp Thr Tyr Ile Val Glu Ala Gly Leu Ala Ser Phe Ile Leu Thr
            260                 265                 270

Ile Lys Phe Gly Ile Glu Thr Met Tyr Pro Ala Leu Gly Leu His Glu
            275                 280                 285

Phe Ala Gly Glu Leu Ser Thr Leu Glu Ser Leu Met Asn Leu Tyr Gln
            290                 295                 300

Gln Met Gly Glu Thr Ala Pro Tyr Met Val Ile Leu Glu Asn Ser Ile
305                 310                 315                 320

Gln Asn Lys Phe Ser Ala Gly Ser Tyr Pro Leu Leu Trp Ser Tyr Ala
            325                 330                 335

Met Gly Val Gly Val Glu Leu Glu Asn Ser Met Gly Gly Leu Asn Phe
            340                 345                 350

Gly Arg Ser Tyr Phe Asp Pro Ala Tyr Phe Arg Leu Gly Gln Glu Met
            355                 360                 365

Val Arg Arg Ser Ala Gly Lys Val Ser Ser Thr Leu Ala Ser Glu Leu
            370                 375                 380

Gly Ile Thr Ala Glu Asp Ala Arg Leu Val Ser Glu Ile Ala Met His
385                 390                 395                 400

Thr Thr Glu Asp Arg Ile Ser Arg Ala Val Gly Pro Arg Gln Ala Gln
            405                 410                 415

Val Ser Phe Leu His Gly Asp Gln Ser Glu Asn Glu Leu Pro Gly Leu
            420                 425                 430

Gly Gly Lys Glu Asp Arg Arg Val Lys Gln Ser Arg Gly Glu Ala Arg
            435                 440                 445

Glu Ser Tyr Arg Glu Thr Glu Ser Ser Arg Ala Ser Asp Ala Arg Ala
            450                 455                 460

Ala His Pro Pro Thr Ser Met Pro Leu Asp Ile Asp Thr Ala Ser Glu
465                 470                 475                 480

Ser Gly Gln Asp Leu Gln Asp Ser Arg Arg Ser Ala Asp Ala Leu Leu
            485                 490                 495

Arg Leu Gln Ala Met Ala Gly Ile Leu Glu Glu Gln Gly Ser Asp Thr
            500                 505                 510

Asp Thr Pro Arg Val Tyr Asn Asp Arg Asp Leu Leu Asp
            515                 520                 525

<210> SEQ ID NO 34
<211> LENGTH: 127
<212> TYPE: PRT
<213> ORGANISM: Measles virus

<400> SEQUENCE: 34

Met His Thr Thr Glu Asp Arg Ile Ser Arg Ala Val Gly Pro Arg Gln
1               5                   10                  15

Ala Gln Val Ser Phe Leu His Gly Asp Gln Ser Glu Asn Glu Leu Pro
            20                  25                  30

Gly Leu Gly Gly Lys Glu Asp Arg Arg Val Lys Gln Ser Arg Gly Glu

-continued

```
        35                  40                  45

Ala Arg Glu Ser Tyr Arg Glu Thr Glu Ser Ser Arg Ala Ser Asp Ala
    50                  55                  60

Arg Ala Ala His Pro Pro Thr Ser Met Pro Leu Asp Ile Asp Thr Ala
65                  70                  75                  80

Ser Glu Ser Gly Gln Asp Leu Gln Asp Ser Arg Arg Ser Ala Asp Ala
                85                  90                  95

Leu Leu Arg Leu Gln Ala Met Ala Gly Ile Leu Glu Glu Gln Gly Ser
            100                 105                 110

Asp Thr Asp Thr Pro Arg Val Tyr Asn Asp Arg Asp Leu Leu Asp
        115                 120                 125

<210> SEQ ID NO 35
<211> LENGTH: 77
<212> TYPE: PRT
<213> ORGANISM: Measles virus

<400> SEQUENCE: 35

Gln Arg Ile Thr Asp Asp Pro Asp Val Ser Ile Arg Leu Leu Glu Val
1               5                   10                  15

Val Gln Ser Asp Gln Ser Gln Ser Gly Leu Thr Phe Ala Ser Arg Gly
            20                  25                  30

Thr Asn Met Glu Asp Glu Ala Asp Gln Tyr Phe Ser His Asp Asp Pro
        35                  40                  45

Ser Ser Ser Asp Gln Ser Arg Ser Gly Trp Phe Glu Asn Lys Glu Ile
    50                  55                  60

Ser Asp Ile Glu Val Gln Asp Pro Glu Gly Phe Asn Met
65                  70                  75
```